US011076838B2

(12) United States Patent
Morimoto et al.

(10) Patent No.: US 11,076,838 B2
(45) Date of Patent: Aug. 3, 2021

(54) ULTRASONIC ENDOSCOPE

(71) Applicant: FUJIFILM Corporation, Tokyo (JP)

(72) Inventors: Yasuhiko Morimoto, Ashigara-kami-gun (JP); Katsuya Yamamoto, Ashigara-kami-gun (JP); Satoru Okada, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 365 days.

(21) Appl. No.: 16/205,369

(22) Filed: Nov. 30, 2018

(65) Prior Publication Data

US 2019/0099163 A1  Apr. 4, 2019

Related U.S. Application Data

(63) Continuation of application No. PCT/JP2017/017858, filed on May 11, 2017.

(30) Foreign Application Priority Data

Jun. 30, 2016 (JP) .............................. JP2016-130382

(51) Int. Cl.
*A61B 8/12* (2006.01)
*A61B 8/00* (2006.01)
*B06B 1/06* (2006.01)

(52) U.S. Cl.
CPC ................ *A61B 8/546* (2013.01); *A61B 8/12* (2013.01); *A61B 8/44* (2013.01); *A61B 8/445* (2013.01);
(Continued)

(58) Field of Classification Search
CPC ........... A61B 8/4483; A61B 8/12; A61B 8/44; A61B 8/4444; A61B 8/445; A61B 8/4488; A61B 8/546; B06B 1/0622
See application file for complete search history.

(56) References Cited

U.S. PATENT DOCUMENTS

2006/0116584 A1  6/2006  Sudol et al.
2008/0300492 A1  12/2008  Nagano et al.
(Continued)

FOREIGN PATENT DOCUMENTS

CN  1725982 A  1/2008
CN  101396289 A  4/2009
(Continued)

OTHER PUBLICATIONS

English translation of Japanese Publication No. 2009-297352-A, published Dec. 24, 2009.
(Continued)

*Primary Examiner* — Mark D Remaly
(74) *Attorney, Agent, or Firm* — Birch, Stewart, Kolasch & Birch, LLP

(57) ABSTRACT

An ultrasonic endoscope has an ultrasonic transducer array in which a plurality of ultrasonic transducers are arranged; a backing material layer on a back side of a plurality of ultrasonic transducers, a wiring board including a plurality of electrode pads that are connected to the plurality of ultrasonic transducers; a plurality of shield cables each including a signal wire and a shield member, a wiring portion in which the plurality of signal wires are electrically connected to the plurality of electrode pads; a ground portion that is electrically connected to the shield members and that have heat conductivity; and a first heat conductive member that extends beyond the backing material layer to a side opposite to the ultrasonic transducer array with respect to the backing material layer and that is thermally connected to the ground portion.

18 Claims, 12 Drawing Sheets

(52) U.S. Cl.
CPC .......... *A61B 8/4444* (2013.01); *A61B 8/4483* (2013.01); *A61B 8/4488* (2013.01); *B06B 1/0622* (2013.01)

(56) References Cited

U.S. PATENT DOCUMENTS

| | | | |
|---|---|---|---|
| 2009/0088646 A1 | 4/2009 | Nagano et al. | |
| 2009/0234233 A1 | 9/2009 | Nagano et al. | |
| 2014/0046190 A1* | 2/2014 | Ogawa | A61B 8/4444 600/462 |

FOREIGN PATENT DOCUMENTS

| | | |
|---|---|---|
| CN | 103300889 A | 9/2013 |
| EP | 0553804 A2 | 8/1993 |
| EP | 0782125 A2 | 7/1997 |
| JP | 2006-25892 A | 2/2006 |
| JP | 2008-295749 A | 12/2008 |
| JP | 2009-297352 A | 12/2009 |
| JP | 5329065 B2 | 10/2013 |
| JP | 5399660 B2 | 1/2014 |
| JP | 2014-57136 A | 3/2014 |
| WO | WO 2014/080312 A1 | 6/2014 |

OTHER PUBLICATIONS

Extended European Search Report dated Apr. 18, 2019, for corresponding European Application No. 17819678.8.
International Preliminary Report on Patentability and Written Opinion of the International Searching Authority (forms PCT/IB/373, PCT/ISA/237 and PCT/IB/326), dated Jan. 10, 2019, for corresponding International Application No. PCT/JP2017/017858, with a Written Opinion translation.
International Search Report (form PCT/ISA/210), dated Jun. 13, 2017, for corresponding International Application No. PCT/JP2017/017858, with an English translation.
Chinese Office Action and Search Report for corresponding Chinese Application No. 201780040177.6, dated Nov. 27, 2020, with English translation of the Office Action.

* cited by examiner

ULTRASONIC ENDOSCOPE

CROSS-REFERENCE TO RELATED APPLICATIONS

This application is a Continuation of PCT International Application No. PCT/JP2017/017858 filed on May 11, 2017, which claims priority under 35 U.S.C. § 119(a) to Japanese Patent Application No. 2016-130382 filed on Jun. 30, 2016. The above application is hereby expressly incorporated by reference, in its entirety, into the present application.

BACKGROUND OF THE INVENTION

1. Field of the Invention

The present invention relates to ultrasonic endoscopes, and, in particular, to an ultrasonic endoscope that has, in a distal end portion thereof, a structure for dissipating heat generated in very small ultrasonic transducers that are used for an ultrasonic endoscope that is inserted into a body cavity.

2. Description of the Related Art

An ultrasonic endoscope is an endoscope that has an ultrasonic observation portion in a distal end portion thereof mainly for the purpose of observing the gallbladder or the pancreas via digestive tract. In the distal end portion of the ultrasonic endoscope, there are heat-generating elements such as ultrasonic transducers and a light source of the endoscope. Because the distal end portion of the ultrasonic endoscope directly contacts the inside of a living body such as a human body, for safety reasons such as prevention of a moderate-temperature burn, it is required that the surface temperature of an insertion portion be lower than or equal to a predetermined temperature.

Moreover, the distal end portion of the ultrasonic endoscope has, in addition to the ultrasonic observation portion, an illumination unit, a suction port, and the like, as with an ordinary endoscope that does not have an ultrasonic observation portion. Therefore, the outside diameter of the distal end portion of the ultrasonic endoscope is large, which causes reduction in operability of the ultrasonic endoscope and increase of a burden on a patient into whom the distal end portion of the ultrasonic endoscope is inserted.

For this reason, an ultrasonic endoscope that has means for lowering the surface temperature of the distal end portion while maintaining the small size of the distal end portion is required. In recent years, various proposals have been made to cool the distal end portion of the ultrasonic endoscope, which is a heat generating source (see JP5329065B and JP5399660B). JP5329065B discloses an ultrasonic endoscope that includes an insertion portion having a bent portion. The insertion portion has a backing material layer having a front surface on which a plurality of ultrasonic transducers are disposed, an exterior member that houses the plurality of ultrasonic transducers at a distal end of the insertion portion, and a heat conductive member that is disposed in the exterior member and that contacts a back surface of the backing material layer and an inner surface of the exterior member. With this structure, heat generated in the ultrasonic transducers and conducted to the backing material layer and heat generated in the backing material layer are conducted to the heat conductive member via the backing material layer, conducted further to the exterior member via the heat conductive member, and dissipated from the exterior member to the outside of the ultrasonic endoscope.

JP5399660B discloses an ultrasonic endoscope that has an exterior member that covers each portion of the ultrasonic endoscope, a backing material layer that is disposed on back surfaces of a plurality of ultrasonic transducers, a signal-wire housing portion that includes a group of shield wires that are electrically connected to the plurality of ultrasonic transducers and a highly heat conductive filler that closely adheres to the backing material layer, and a highly heat conductive layer that is disposed in contact with the signal-wire housing portion and the exterior member. With this structure, heat generated in the ultrasonic transducers is diffused to the filler via a back surface of the backing material layer or the group of shield wires, and the heat of the filler is further diffused to the surface of the exterior member via the highly heat conductive layer.

SUMMARY OF THE INVENTION

The technology disclosed in JP5329065B takes into consideration only a heat dissipation path that dissipates heat generated in the ultrasonic transducers and the backing material layer to the exterior member via the heat conductive member. The technology disclosed in JP5399660B takes into consideration only a heat dissipation path that dissipates heat generated in the ultrasonic transducers to the exterior member via the backing material layer and the highly heat conductive layer that is in contact with the filler. Thus, each of the technologies disclosed in JP5329065B and JP5399660B, which takes into consideration only the heat dissipation path to the exterior member, has a problem in that further improvement of heat dissipation efficiency cannot be expected. Moreover, because each of the technologies disclosed in JP5329065B and JP5399660B uses only the heat dissipation path to the exterior member, heat is dissipated to the inside of a body cavity near the distal end portion of the ultrasonic endoscope.

Therefore, the technologies have a problem in that, in a case where the drive voltage of the ultrasonic transducers is increased, the temperature of a region around the distal end portion of the ultrasonic endoscope is increased.

Examples of means that need to be used to improve the diagnosis accuracy in ultrasonic diagnosis with the ultrasonic endoscope disclosed in JP5329065B or JP5399660B include increasing ultrasound transmitting power by laminating ultrasonic transducers, increasing sensitivity in receiving an ultrasonic echo by increasing the number of ultrasonic transducers, and increasing the drive voltage of the plurality of ultrasonic transducers. When such means is used, the amount of heat dissipated from the plurality of ultrasonic transducers increases, and therefore the heat causes an increase in the temperature of the insertion portion of the ultrasonic endoscope that contacts the inner wall of a body cavity of a patient, in particular, the temperature of the surface of the distal end portion of the ultrasonic endoscope in which the plurality of ultrasonic transducers are disposed.

There is a problem in that, although improvement of accuracy in ultrasonic diagnosis is required in addition to improvement of operability and relieving of a burden on a patient, it is very difficult to efficiently dissipate heat generated in the distal end portion of the ultrasonic endoscope while maintaining the small diameter of the insertion portion of the ultrasonic endoscope and maintaining the small size of the distal end portion.

An object of the present invention is to solve the problems of the existing technology described above and to provide an ultrasonic endoscope that has a heat dissipation structure that can efficiently dissipate heat generated in ultrasonic transducers while maintaining the small diameter of an insertion portion and maintaining the small size of a distal end portion, and, as a result, that can improve the diagnosis accuracy in ultrasonic diagnosis.

In order to achieve the object, an ultrasonic endoscope according to the present invention includes a laminated body that includes an ultrasonic transducer array in which a plurality of ultrasonic transducers are arranged, and a backing material layer that is disposed on a back surface side of the plurality of ultrasonic transducers; a wiring board that includes a plurality of electrode pads each of which is electrically connected to a corresponding one of the plurality of ultrasonic transducers of the ultrasonic transducer array; a plurality of shield cables that include a plurality of signal wires each of which is electrically connected to a corresponding one of the plurality of ultrasonic transducers, and shield members for the plurality of signal wires; a wiring portion that includes a plurality of connection portions at each which a corresponding one of the plurality of signal wires of the plurality of shield cables is electrically connected to a corresponding one of the plurality of electrode pads of the wiring board; a ground portion that is electrically connected to the shield members of the shield cables and that has heat conductivity; and a first heat conductive member that is disposed on a side surface of the laminated body that includes the ultrasonic transducer array and the backing material layer, that extends beyond the backing material layer to a side opposite to the ultrasonic transducer array with respect to the backing material layer, and that is thermally connected to the ground portion.

Preferably, the first heat conductive member is folded back toward the side surface side of the laminated body and is connected to the ground portion.

Preferably, the first heat conductive member is an electroconductive member; the wiring board is disposed on the laminated body side with respect to the first heat conductive member; and, in a region in which the first heat conductive member covers at least the plurality of connection portions of the wiring portion of the wiring board, the ultrasonic endoscope has an insulating layer between the first heat conductive member and the plurality of connection portions.

Preferably, the insulating layer is removed at least at a portion where the first heat conductive member is connected to the ground portion.

Preferably, the first heat conductive member has, in a portion extending beyond the backing material layer to the side opposite to the ultrasonic transducer array with respect to the backing material layer, a shape that covers at least a part of a side surface of the wiring board.

Preferably, in a portion extending beyond the backing material layer to the side opposite to the ultrasonic transducer array with respect to the backing material layer, the first heat conductive member is bent so as to surround the wiring portion and the ground portion and is connected to the ground portion.

Preferably, the first heat conductive member is an electroconductive member, and the first heat conductive member and the ground portion are connected to each other by using a solder or a silver paste.

Preferably, a plurality of the wiring boards are disposed in a portion that is beyond the backing material layer on the side opposite to the ultrasonic transducer array with respect to the backing material layer.

Preferably, the shield members of the plurality of shield cables are made of a metal; and the ground portion is a collective ground portion to which the shield members of the plurality of shield cables are electrically connected, a ground bar that is provided in the wiring portion and to which the shield members are electrically connected, or a ground pad that is provided in the wiring board and that is electrically connected to the ground bar.

Preferably, a melting point of a solder that is used to connect the first heat conductive member to the collective ground portion, the ground bar, or the ground pad is lower than a melting point of a solder that is used to connect the collective ground portion, the ground bar, or the ground pad to the shield members of the plurality of coaxial cables.

Preferably, the ground bar or the ground pad is provided on at least one of a front surface of the wiring board that is a surface on the first heat conductive member side, a back surface of the wiring board that is on a back side of the front surface, or both end surfaces of the front surface and the back surface of the wiring board; and the first heat conductive member is connected to the ground bar or the ground pad.

Preferably, a plurality of the wiring boards are disposed in a portion that is beyond the backing material layer on the side opposite to the ultrasonic transducer array with respect to the backing material layer; and, among the plurality of wiring boards, the ground bars or the ground pads of the wiring boards that are disposed adjacent to each other are thermally connected by using a second heat conductive member that is independent from the first heat conductive member.

Preferably, a plurality of the wiring boards are disposed in a portion that is beyond the backing material layer on the side opposite to the ultrasonic transducer array with respect to the backing material layer, at least one of the wiring boards on a central side connects the first heat conductive member to the ground bar or the ground pad on the central side or an end surface side of the wiring board, and at least one of the wiring boards on an outer side connects the first heat conductive member to the ground bar or the ground pad on the outer side or on an end surface side of the wiring board.

Preferably, among the plurality of wiring boards, the ground bars or the ground pads of the wiring boards that are disposed adjacent to each other are thermally connected by using a second heat conductive member that is independent from the first heat conductive member.

Preferably, the first heat conductive member is composed of two first heat conductive members that are disposed on both side surfaces of the laminated body and that are connected to each other by using a third heat conductive member.

With the present invention, because the distal end portion of the ultrasonic endoscope has a heat dissipation structure, it is possible to efficiently dissipate heat that is generated due to driving of the ultrasonic transducers, and it is possible to increase the output power of the ultrasonic transducers without increasing a burden on a patient.

DESCRIPTION OF THE PREFERRED EMBODIMENTS

First Embodiment

Figure 1:
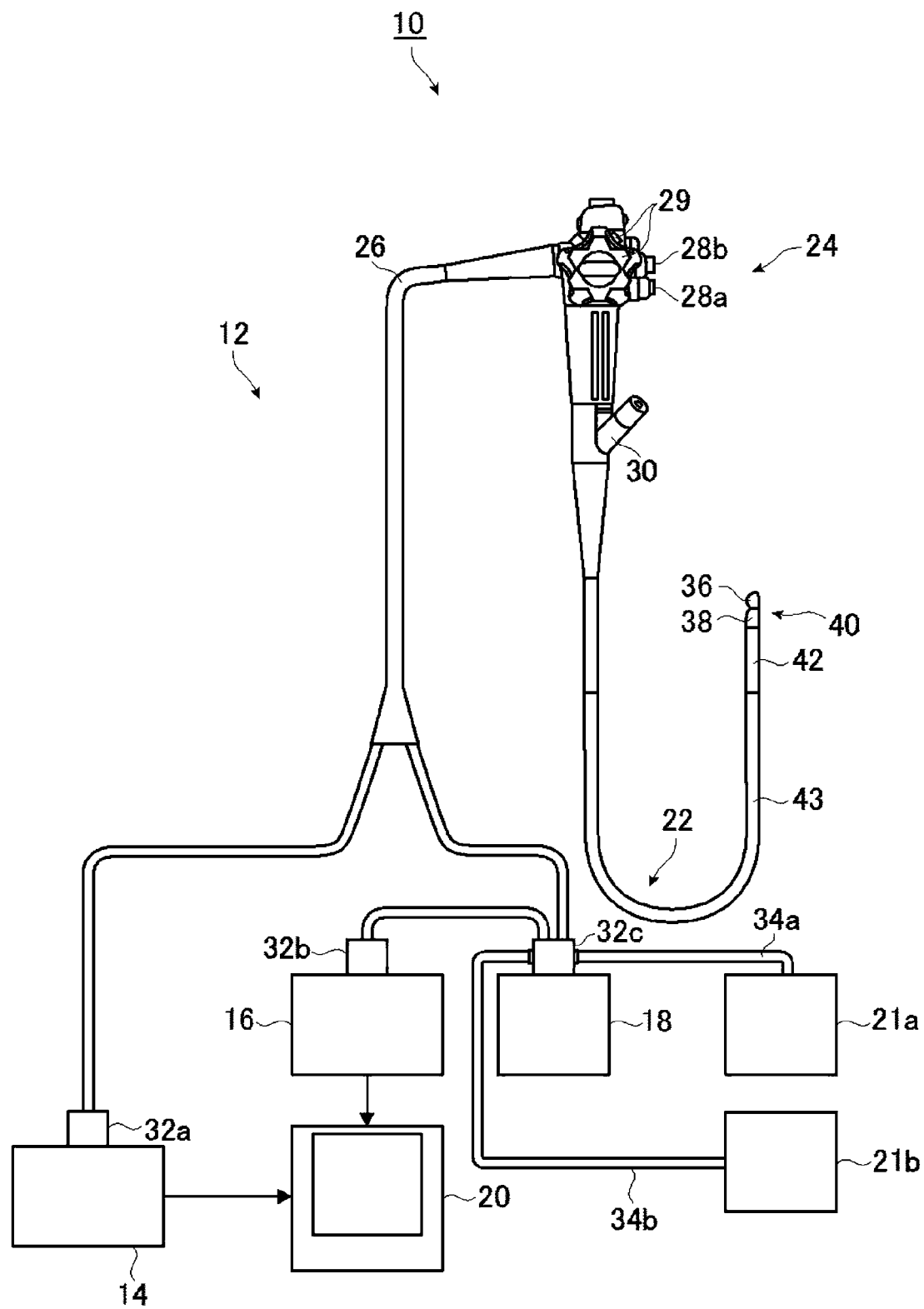
FIG. 1 is a schematic view of an example of the structure of an ultrasonic inspection system that uses an ultrasonic endoscope to which an ultrasonic transducer unit according to the present invention is applied.

Hereinafter, an ultrasonic endoscope according to the present invention will be described in detail based on preferred embodiments illustrated in the drawings.

FIG. 1 is a schematic view of an example of the structure of an ultrasonic inspection system that uses the ultrasonic endoscope according to the present invention.

An ultrasonic inspection system 10 shown in FIG. 1 is a system that enables observation of the gallbladder or the pancreas, which is difficult to observe by using ultrasonic inspection from the body surface of a subject such as a patient, via digestive tract such as the esophagus, the stomach, the duodenum, the small intestine, the large intestine, and the like, each of which is a body cavity of the subject. The ultrasonic inspection system 10 inserts an ultrasonic endoscope 12 according to the present invention, which has an ultrasonic observation portion 36 that captures an ultrasound tomographic image (hereinafter, referred to an ultrasound image) and an endoscopic observation portion 38 that captures an endoscopic optical image (hereinafter, referred to as an endoscopic image), into a body cavity of a subject and captures the ultrasound image of an observation target site of the subject while observing the endoscopic image of the subject.

As illustrated in FIG. 1, the ultrasonic inspection system 10 includes the ultrasonic endoscope 12 having a heat dissipation structure that is a feature of the present invention, an ultrasonic processor device 14 that generates an ultrasound image, an endoscope processor device 16 that generates an endoscopic image, a light source device 18 that supplies illumination light for illuminating the inside of a body cavity to the ultrasonic endoscope 12, and a monitor 20 that displays the ultrasound image and/or the endoscopic image.

The ultrasonic inspection system 10 further includes a water supply tank 21a that stores cleaning water or the like and a suction pump 21b that suctions a suction object (including the supplied cleaning water and the like) in a body cavity. Although not illustrated, the ultrasonic inspection system 10 may include a supply pump or the like that supplies cleaning water in the water supply tank 21a or a gas, such as outside air, to a pipe line (not shown) in the ultrasonic endoscope 12.

First, the ultrasonic endoscope 12 shown in FIG. 1 has, at the distal end thereof, the ultrasonic observation portion 36, having a heat dissipation structure that is a feature of the present invention, and the endoscopic observation portion 38. The ultrasonic endoscope 12 captures an ultrasound image (echo signal) and an endoscopic image (image signal) of the inside of the body cavity.

The ultrasonic endoscope 12 is composed of an insertion portion 22 that includes the ultrasonic observation portion 36 and the endoscopic observation portion 38 at an end thereof and that is inserted into a body cavity of a subject; an operating unit 24 that is connected to a proximal end portion of the insertion portion 22 and with which an operator, such as a doctor or an engineer, performs an operation; and a universal cord 26 one end of which is connected to the operating unit 24.

The operating unit 24 has an air/water supply button 28a, for opening or closing an air/water supply pipe line (not shown) from the water supply tank 21a, and a suction button 28b, for opening or closing a suction pipe line (not shown) from the suction pump 21b, which are arranged side by side. Moreover, the operating unit 24 has a pair of angle knobs 29 and a treatment tool insertion port 30 (forceps port).

Here, the water supply tank 21a stores cleaning water or the like that is supplied to the air/water supply pipe line in the ultrasonic endoscope 12 for cleaning the endoscopic observation portion 38 of the ultrasonic endoscope 12 and the like. The air/water supply button 28a is used to eject a gas such as air and water such as cleaning water, which are supplied from the water supply tank 21a through the air/water supply pipe line, from the endoscopic observation portion 38 on the distal end side of the insertion portion 22.

The suction pump 21b suctions a suction pipe line (not shown) to suction a suction object (including supplied cleaning water and the like) in a body cavity from the distal end side of the ultrasonic endoscope 12. The suction button 28b is used to suction a suction object in a body cavity from the distal end side of the insertion portion 22 by using a suction force of the suction pump 21b.

The treatment tool insertion port 30 is used to insert a treatment tool, such as forceps, a puncture needle, a high-frequency knife, or the like.

At the other end portions of the universal cord 26, an ultrasound connector 32a connected to the ultrasonic processor device 14, an endoscope connector 32b connected to the endoscope processor device 16, and a light source connector 32c connected to the light source device 18 are provided. The ultrasonic endoscope 12 is removably connected to the ultrasonic processor device 14, the endoscope processor device 16, and the light source device 18 via the connectors 32a, 32b, and 32c, respectively. An air/water supply tube 34a, for connecting to the water supply tank 21a, a suction tube 34b, for connecting the suction pump 21b, and the like are connected to the light source connector 32c.

The insertion portion 22 is composed of, in order from the distal end side, a distal end portion 40 (distal end rigid portion) that is formed of a rigid member and that has the ultrasonic observation portion 36 and the endoscopic observation portion 38; a bending portion 42 that is connected to the proximal end side of the distal end portion 40, that is formed by coupling a plurality of bending pieces, and that can be bent freely; and a soft portion 43 that couples the proximal end side of the bending portion 42 and the distal end side of the operating unit 24 to each other, that has a thin and elongated shape, and that has flexibility.

The bending portion 42 is remote-controlled so as to be bent by rotating the pair of angle knobs 29 of the operating unit 24. Thus, the distal end portion 40 can be directed in a desired direction.

A balloon, which covers the ultrasonic observation portion 36 and into which an ultrasound transmission medium (such as water, oil, or the like) is injected, may be removably attached to the distal end portion 40. Because ultrasound and an echo signal are considerably attenuated in air, by inflating the balloon by injecting the ultrasound transmission medium into the balloon and causing the balloon to contact an observation target site, it is possible to remove air from a space between an ultrasonic transducer array 50 (see FIGS. 2 to 4) of the ultrasonic observation portion 36 and the observation target site and to prevent attenuation of the ultrasound and the echo signal.

The ultrasonic processor device 14 generates and supplies an ultrasound signal (data), for generating ultrasound, to the ultrasonic transducer array 50 (see FIGS. 2 to 4, 7, and 8) of an ultrasonic transducer unit 46 (see FIGS. 2 to 4, 7, and 8) of the ultrasonic observation portion 36 of the distal end portion 40 of the insertion portion 22 of the ultrasonic endoscope 12. Moreover, the ultrasonic processor device 14 receives and obtains an echo signal (data), which is reflected from an observation target site to which ultrasound is emitted, with the ultrasonic transducer array 50; and generates an ultrasound image, which is to be displayed on the monitor 20, by performing various types of signal (data) processing on the obtained echo signal.

The endoscope processor device 16 receives and obtains a captured image signal (data) that is obtained from an observation target site, which is illuminated with illumination light from the light source device 18, in the endoscopic observation portion 38 of the distal end portion 40 of the insertion portion 22 of the ultrasonic endoscope 12. The endoscope processor device 16 generates an endoscopic image, which is to be displayed on the monitor 20, by performing various types of signal (data) processing on the obtained image signal.

The processor devices 14 and 16 may be composed of a processor such as a personal computer (PC).

In order to obtain an image signal by capturing an image of an observation target site in a body cavity by using the endoscopic observation portion 38 of the ultrasonic endoscope 12, the light source device 18 generates illumination light, such as white light or a specific wavelength light, composed of three primitive color light that is, for example, red light (R), green light (G), and blue light (B), and supplies the illumination light to the ultrasonic endoscope 12. The illumination light propagates via a light guide (not shown) or the like in the ultrasonic endoscope 12, is emitted from the endoscopic observation portion 38 of the distal end portion 40 of the insertion portion 22 of the ultrasonic endoscope 12, and illuminates the observation target site in the body cavity.

The monitor 20 receives image signals generated by the ultrasonic processor device 14 and the endoscope processor device 16 and displays an ultrasound image and an endoscopic image. An image to be displayed on the monitor 20 can be switched between the ultrasound image and the endoscopic image, and both of these images can be simultaneously displayed on the monitor 20. A monitor for displaying the ultrasound image and a monitor for displaying an endoscopic image may be independently provided, or the ultrasound image and the endoscopic image may be displayed in any other appropriate form.

Next, referring to FIGS. 2 to 4, the structure of the distal end portion 40 of the insertion portion 22 of the ultrasonic endoscope 12 according to the present embodiment of will be described in detail.

Figure 2:
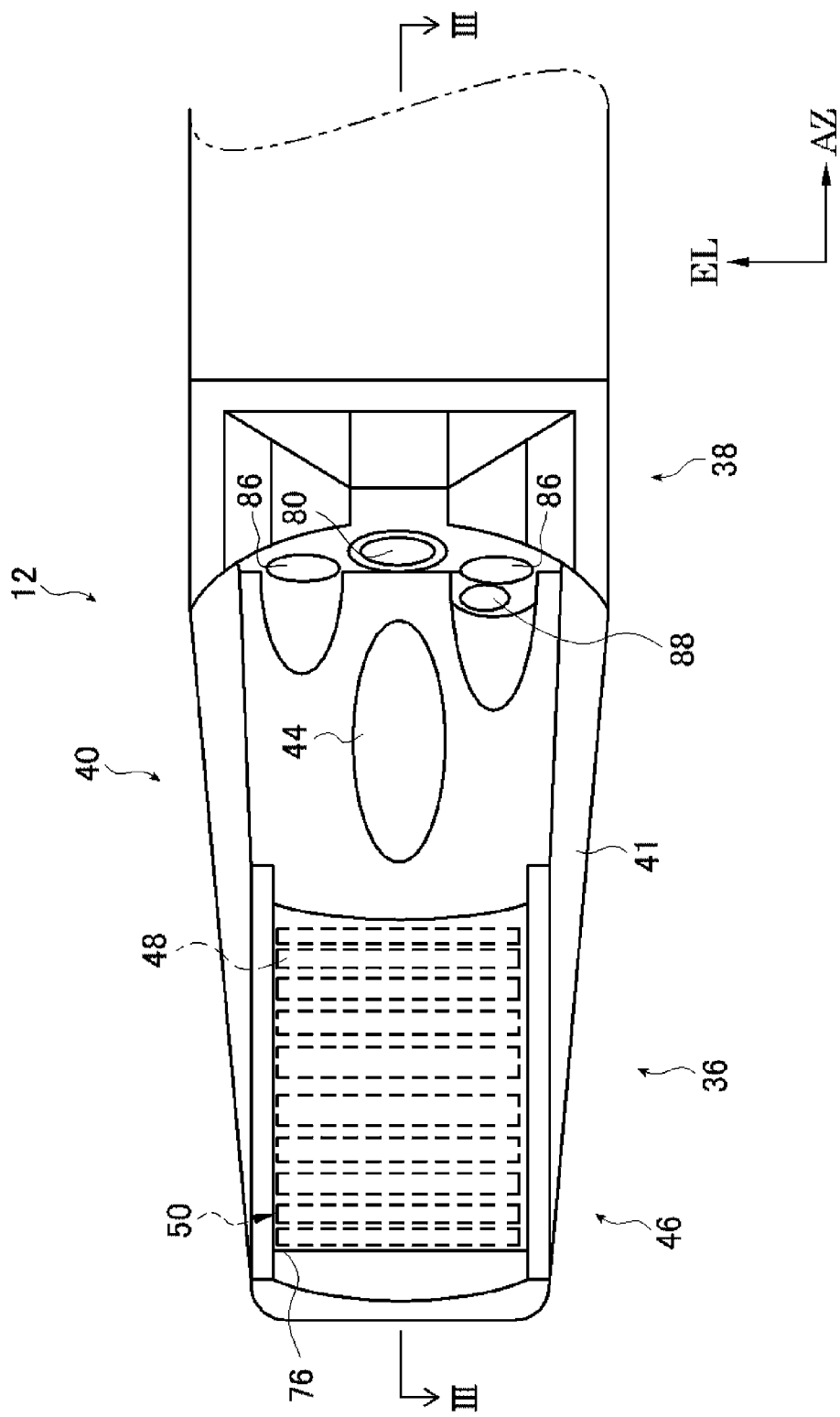
FIG. 2 is a partial enlarged plan view of a distal end portion of the ultrasonic endoscope shown in FIG. 1.

FIG. 2 is a partial enlarged plan view of the distal end portion of the ultrasonic endoscope shown in FIG. 1 and the vicinity of the distal end portion. FIG. 3 is a partial longitudinal sectional view taken along line III-III in FIG. 2, illustrating the distal end portion of the ultrasonic endoscope shown in FIG. 2 that is cut along the centerline in the longitudinal direction thereof FIG. 4 is a cross-sectional view taken along line IV-IV in FIG. 3, illustrating an ultrasonic transducer array of an ultrasonic observation portion of the distal end portion of the ultrasonic endoscope shown in FIG. 3 that is cut along the centerline of an arc structure. Here, FIG. 4 is simplified for convenience of description, and coaxial cables 56 (see FIG. 3) are omitted. As illustrated in FIGS. 2, and 3, the distal end portion 40 of the ultrasonic endoscope 12 has the ultrasonic observation portion 36, for obtaining an ultrasound image, on the distal end side; the endoscopic observation portion 38, for obtaining an endoscopic image, on the proximal end side; and a treatment tool lead-out port 44 between these. The observation portions 36 and 38 are attached to and held by an exterior member 41 that is the body of the distal end portion 40 of the ultrasonic endoscope 12 and that is made of a rigid material such as a rigid resin.

In the example shown in FIG. 2, the treatment tool lead-out port 44 is formed between the ultrasonic observation portion 36 and the endoscopic observation portion 38. However, the present invention is not particularly limited to the example illustrated in the figure. The treatment tool lead-out port 44 may be formed in the endoscopic observation portion 38 or may be formed on the proximal end side (the bending portion 42 side) relative to the endoscopic observation portion 38.

Figure 3:
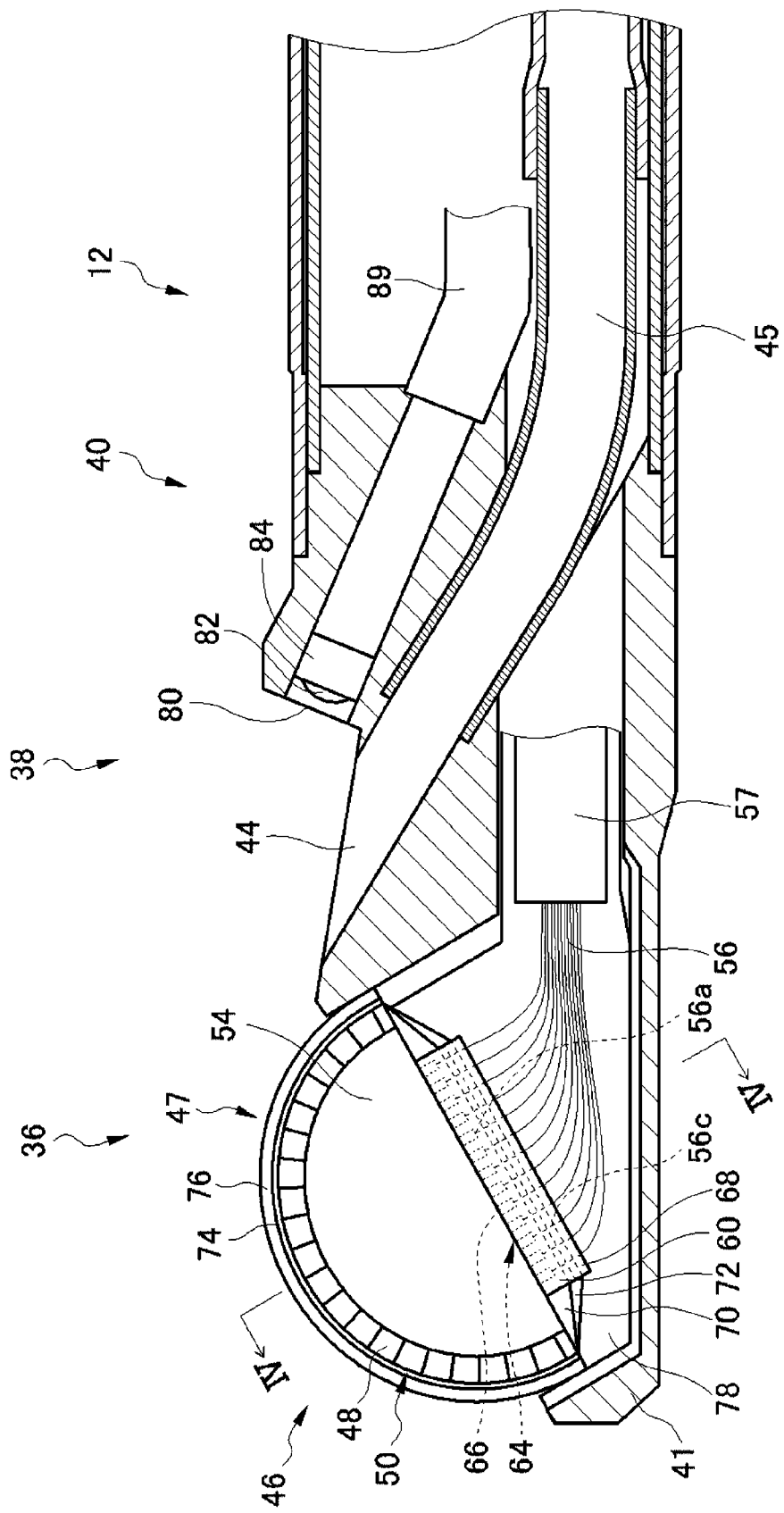
FIG. 3 is a partial longitudinal sectional view taken along line III-III in FIG. 2, illustrating the distal end portion of the ultrasonic endoscope shown in FIG. 2.
Figure 4:
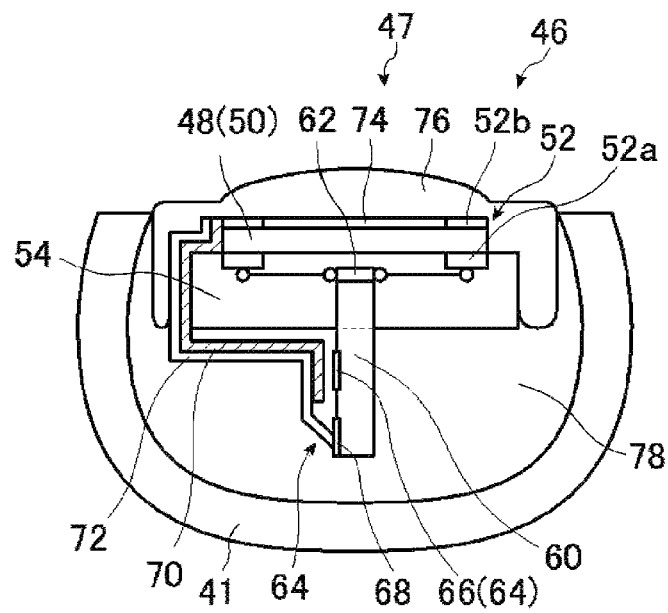
FIG. 4 is a cross-sectional view taken along line IV-IV in FIG. 3, illustrating an example of an ultrasonic transducer unit of an ultrasonic observation portion of the distal end portion of the ultrasonic endoscope shown in FIG. 3.

As illustrated in FIGS. 2 to 4, the ultrasonic observation portion 36 is composed of the ultrasonic transducer unit 46 and the exterior member 41 for attaching and holding the ultrasonic transducer unit 46.

The ultrasonic transducer unit 46 has the ultrasonic transducer array 50 that is composed of a plurality of ultrasonic transducers 48, an electrode portion 52 that is disposed at an end portion side of the ultrasonic transducer array 50 in the width direction, a backing material layer 54 that supports the ultrasonic transducers 48 of the ultrasonic transducer array 50 from the lower surface side, a wiring board 60 that is embedded in the backing material layer 54 and that is electrically connected to the electrode portion 52, an insulating layer 70 that is disposed along a side surface of the backing material layer 54 in the width direction, a copper foil 72 (first heat conductive member) that is disposed on a side surface side of the backing material layer 54 in the width direction and along a side opposite to the backing material layer 54 with respect to the insulating layer 70, and a filler layer 78 that fills a space between the exterior member 41 and the backing material layer 54.

In the example shown in FIG. 4, one end side of the wiring board 60 is embedded in the backing material layer 54; and a portion of the wiring board 60 embedded in the backing material layer 54 and the electrode portion 52, which is electrically continuous with a plurality of ultrasonic transducers 48, are electrically connected to each other. Moreover, although not illustrated in FIG. 4, the plurality of coaxial cables 56 are electrically connected to a portion of the wiring board 60 on a side opposite to the plurality of ultrasonic transducers 48 with respect to the backing material layer 54 (the lower side the backing material layer 54).

Figure 5:
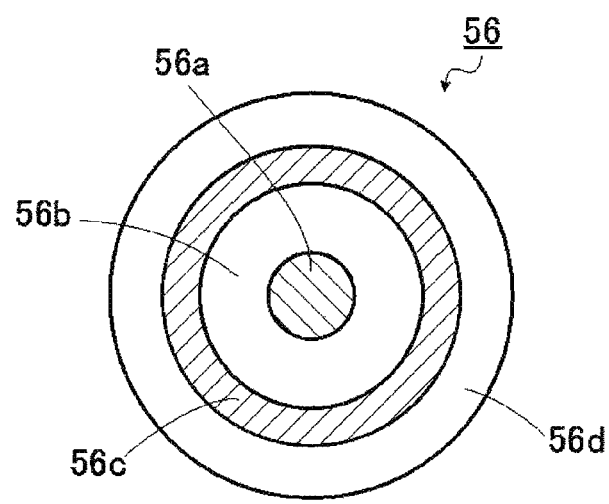
FIG. 5 is a schematic cross-sectional view of a coaxial cable shown in FIG. 3.

As illustrated in FIG. 3, the plurality of coaxial cables 56, one end of each of which is electrically connected to the wiring board 60, are bundled together by using a jacket 57 on the proximal end side (the universal cord 26 side) of the distal end portion 40 of the insertion portion 22. When forming wiring, each of the coaxial cables 56 is drawn out and electrically connected to the wiring board 60. As illustrated in FIG. 5, each of the plurality of coaxial cables 56 has a signal wire 56a that is on the central side thereof and that is electrically connected to a corresponding one of a plurality of connection portions 66 of a wiring portion 64 of the wiring board 60 (described below), an insulating jacket 56b that is disposed in a layer outside of the signal wire 56a, an electroconductive shield layer 56c that is disposed in a layer outside of the jacket 56b and that can be grounded on the proximal end side (the universal cord 26 side) of the ultrasonic endoscope 12, and an insulating jacket 56d that is disposed in the outermost layer. Therefore, as in the example shown in FIG. 3, in the case where the wiring portion 64, to which the signal wires 56a are to be electrically connected, is disposed on the backing material layer 54 side relative to a ground bar 68 (described below) in the wiring board 60, it is possible to connect the signal wires 56a of the plurality of coaxial cables 56 to the wiring portion 64 of the wiring board 60 in such a way that the plurality of coaxial cables 56 are not bent.

Here, the meaning of "grounding" in the present invention is not limited to causing the potential of an electroconductive member to be zero, and also includes a case of, for example, maintaining an electroconductive member at a predetermined low potential by connecting the electroconductive member to a member having a large electric capacity.

In the example shown in FIG. 3, the coaxial cables 56 are used. However, cables (shield cables) that have structures different from the coaxial cables 56 may be used, provided that the cables each have a signal wire, for transmitting/receiving a voltage signal by being electrically connected to a corresponding one of the plurality of ultrasonic transducers 48, and a shield member that can be can be grounded by being electrically connected to a transducer ground 52b (described below) of the plurality of ultrasonic transducers 48. For example, although not illustrated, as the shield cable, it is possible to use a cable having a known structure, such as a cable unit that includes, on the central side thereof, a plurality of signal wires covered by an insulating jacket and a plurality of lead wires that can be grounded; and has a jacket that covers the plurality of signal wires and the lead wires. The arrangement of the signal wires and the lead wires of the cable unit is not limited to the one described above. The plurality of signal wires and lead wires may be randomly arranged in an outer jacket that covers these wires.

The ultrasonic transducer unit 46 further has an acoustic matching layer 74 that is laminated on the ultrasonic transducer array 50, and an acoustic lens 76 that is laminated on the acoustic matching layer 74. That is, the ultrasonic transducer unit 46 is composed of a laminated body 47 in which the acoustic lens 76, the acoustic matching layer 74, the ultrasonic transducer array 50, and the backing material layer 54 are laminated.

The acoustic matching layer 74 performs acoustic impedance matching between a subject, such as a human body, and the ultrasonic transducers 48.

The acoustic lens 76, which is attached onto the acoustic matching layer 74, causes ultrasound, which is emitted from the ultrasonic transducer array 50, to converge toward an observation target site. The acoustic lens 76 is made of, for example, a silicone-based resin (a millable silicone rubber (HTV rubber), a liquid silicone rubber (RTV rubber), or the like), a butadiene-based resin, a polyurethane-based resin, or the like. In order to perform acoustic impedance matching between a subject and the ultrasonic transducers 48 by using the acoustic matching layer 74 and to increase transmittance of ultrasound, powder of titanium oxide, alumina, silica, or the like is mixed into the acoustic lens 76 as necessary.

The ultrasonic transducer array 50 of the ultrasonic transducer unit 46 is, for example, an array of 48 to 192 channels (CH) that is composed of 48 to 192 pieces of rectangular-parallelepiped-shaped ultrasonic transducers 48 that are arranged in an outwardly convex arc shape.

That is, the ultrasonic transducer array 50 is formed by arranging the plurality of ultrasonic transducers 48, for example, in a one-dimensional array shape at a predetermined pitch as in the example shown in the figures. Thus, the ultrasonic transducers 48 of the ultrasonic transducer array 50 are arranged at a regular pitch in the axial direction of the distal end portion 40 (the longitudinal axial direction of the insertion portion 22) in a convexly curved shape and are sequentially driven on the basis of drive signals that are input from the ultrasonic processor device 14. Thus, convex electronic scan is performed over a scan range that is a range in which the ultrasonic transducers 48 are arranged as shown in FIG. 2.

The length of the ultrasonic transducer array 50 in the width direction of the ultrasonic transducer array 50, that is, the longitudinal direction of the ultrasonic transducers 48 (elevation (EL) direction) is smaller than the length of the ultrasonic transducer array 50 in a direction parallel to the bottom surface of the backing material layer 54 (the azimuth (AZ) direction). The ultrasonic transducer array 50 is disposed so as to be inclined in such a way that the back end side thereof protrudes. As illustrated in FIG. 4, the ultrasonic transducer 48 has a structure in which, for example, electrodes are formed on both surfaces of a thick piezoelectric film of lead zirconate titanate (PZT), polyvinylidene fluoride (PVDF), or the like. One of the electrodes is an individual electrode 52a that is independently provided in each ultrasonic transducer 48, and the other electrode is the transducer ground 52b (transducer ground electrode), which is common to all of the ultrasonic transducers 48. In the example shown in the figures, a plurality of the individual electrodes 52a are disposed on the lower surfaces of end portions of the plurality of ultrasonic transducers 48, and the transducer ground 52*b* is disposed on the upper surfaces of the end portions of the ultrasonic transducers 48. The plurality of individual electrodes 52*a* and the transducer ground 52*b* constitute the electrode portion 52.

Each gap between two adjacent ultrasonic transducers 48 is filled with a filler, such as an epoxy resin or the like.

In the ultrasonic transducer unit 46 of the ultrasonic observation portion 36, when each of the ultrasonic transducers 48 of the ultrasonic transducer array 50 is driven and a voltage is applied to both electrodes of the ultrasonic transducer 48, the piezoelectric body vibrate and successively generates ultrasound, and the ultrasound is emitted toward an observation target site of a subject. By successively driving the plurality of ultrasonic transducers 48 by using an electronic switch such as a multiplexer, ultrasound is scanned over a scan range along a curved surface on which the ultrasonic transducer array 50 is disposed, such as a range of about several tens of millimeters from the center of curvature of the curved surface.

When receiving an echo signal (ultrasonic echo) reflected from the observation target site, the piezoelectric body vibrates and generates a voltage, and this voltage is output to the ultrasonic processor device 14 as an electric signal corresponding to the received ultrasonic echo (ultrasound detection signal). The ultrasonic processor device 14 performs various types of signal processing on the electric signal, and then an ultrasound image is displayed on the monitor 20.

Heat is generated in each of piezoelectric bodies of the plurality of ultrasonic transducers 48 when, as described above, a drive voltage is applied to the plurality of ultrasonic transducers 48 and the piezoelectric bodies of the plurality of ultrasonic transducers 48 vibrate and generate ultrasound emitted toward a target object, and when the plurality of ultrasonic transducers 48 receive an ultrasonic echo of ultrasound, which has been emitted from the plurality of ultrasonic transducers 48 and reflected by the target, and the piezoelectric bodies vibrates and generate an ultrasonic echo signal (voltage signal). One of means for increasing the resolution of an ultrasound image, that is, for improving accuracy in ultrasonic diagnosis is means of increasing the power of drive signals (voltage signals) of the plurality of ultrasonic transducers 48. However, as the drive voltage increases, heat generated in the piezoelectric body increases. Therefore, by providing a heat dissipation structure that is a feature of the present invention in the distal end portion 40 of the ultrasonic endoscope 12, it is possible to efficiently dissipate heat generated in the piezoelectric body and to improve accuracy in ultrasonic diagnosis.

As illustrated in FIGS. 3 and 4, the electrode portion 52 of the ultrasonic transducer unit 46 is disposed in an arc shape on an end surface side of the ultrasonic transducer array 50 (the ultrasonic transducers 48), which is perpendicular to an arc-shaped surface formed due to arrangement of the plurality of (48 to 192) ultrasonic transducers 48. The electrode portion 52 is composed of a plurality of (48 to 192) individual electrodes 52*a* each of which is electrically continuous with a corresponding one of the plurality of (48 to 192) ultrasonic transducers 48. The electrode portion 52 includes the transducer ground 52*b* of the plurality of ultrasonic transducers 48. Here, in the present invention, the meaning of the term "perpendicular" is not limited to "90 degrees" and includes the meaning of "substantially perpendicular", such as "90 degrees ±5 degrees", that is, "the range of 85 degrees to 95 degrees".

The electrode portion 52 is disposed on an end surface side of the ultrasonic transducer array 50, which is perpendicular to the surface on which the ultrasonic transducers 48 are arranged. In a case where the number of ultrasonic transducers 48 is small, the electrode portion 52 may be disposed on only one end surface side. Because the number of ultrasonic transducers 48 is preferably large, the plurality of individual electrodes 52*a* are preferably disposed on both outer surfaces of the ultrasonic transducer array 50. The plurality of individual electrodes 52*a* may be disposed on the central side, instead of the end surface side, of the ultrasonic transducer array 50. For example, in a case where the ultrasonic transducers 48 are arranged in a plurality of rows, such as in two rows in the width direction, by disposing the plurality of individual electrodes 52*a* on the central side of the ultrasonic transducer array 50, wiring can be efficiently formed even when the number of channels is large. In this way, by disposing the plurality of individual electrodes 52*a* on the central side in addition to on both outer surfaces of the ultrasonic transducer array 50, the number of ultrasonic transducers 48, that is, the number of channels can be further increased.

In the example shown in FIG. 4, the plurality of individual electrodes 52*a* are the individual electrodes 52*a* that are disposed on the end surface side of the longitudinal direction of the ultrasonic transducers 48. However, the present invention is not limited to this. In any of the cases where the individual electrodes 52*a* are disposed on one outer surface, both outer surfaces, and the central side of the ultrasonic transducer array 50, the individual electrodes may be other electrodes that are connected from the individual electrode 52*a* through wiring, provided that the other electrodes are electrically continuous with the individual electrodes 52*a* of the ultrasonic transducers 48. The electrode portion 52 directly includes the transducer ground 52*b*. However, the electrode portion 52 may include an electrode that is connected from the transducer ground 52*b* through wiring.

Preferably, the plurality of individual electrodes 52*a* and the transducer ground 52*b* of the electrode portion 52 are formed as electrode pads.

Next, as shown in FIGS. 3 and 4, the backing material layer 54 of the ultrasonic transducer unit 46 is a layer that is made of a backing material and that is disposed inside with respect to the arrangement surface of the plurality of ultrasonic transducers 48, that is, on the back surface (lower surface) of the ultrasonic transducer array 50. Accordingly, the backing material layer 54 has a function of mechanically and softly supporting the ultrasonic transducer array 50 and a function of attenuating, among ultrasound signals emitted from the plurality of ultrasonic transducers 48 or reflected and propagated from an observation target, ultrasound that has propagated to the backing material layer 54 side. Therefore, the backing material is a material having rigidity, such as a rigid rubber, to which an ultrasound attenuation material (such as ferrite or a ceramic) is added as necessary.

Accordingly, preferably, the ultrasonic transducer array 50 is an array in which the plurality of ultrasonic transducers 48 each having a rectangular-parallelepiped shape in the example shown in the figures are arranged at a regular pitch on the arc-shaped upper surface of the backing material layer 54, which is an upper surface having a convex arc-shaped cross section, in such a way that the longitudinal directions of the plurality of ultrasonic transducers 48 are parallel to each other, that is, an array in which the plurality of ultrasonic transducers 48 are arranged in an arc shape so as to face outward.

The shape of the backing material layer 54 may be any appropriate shape that does not impair the functions described above. The backing material layer 54 may have a substantially semi-cylindrical shape shown in FIGS. 3 and 4, and may have a recessed portion so that a part of the wiring board 60 can be housed therein.

The filler layer 78 of the ultrasonic transducer unit 46 fills the space between the exterior member 41 and the backing material layer 54. The filler layer 78 also has a function of fixing the wiring board 60, the signal wires 56a of the coaxial cables 56, the copper foil 72, and various wiring portions. Preferably, the acoustic impedance of the filler layer 78 matches the acoustic impedance of the backing material layer 54 with an accuracy of a predetermined degree or higher so that a boundary surface between the filler layer 78 and the backing material layer 54 may not reflect an ultrasound signal propagated from the ultrasonic transducer array 50 to the backing material layer 54 side. Moreover, preferably, the filler layer 78 has heat dissipation ability in order to increase the efficiency in dissipating heat generated in the plurality of ultrasonic transducers 48. When the filler layer 78 has heat dissipation ability, because heat is received from the backing material layer 54, the wiring board 60, the copper foil 72, and the shield layers 56c of the coaxial cables 56, heat dissipation efficiency can be improved.

The wiring board 60 of the ultrasonic transducer unit 46 is disposed on the laminated body 47 side with respect to the copper foil 72, which is a heat conductive member. The laminated body 47 is composed of the ultrasonic transducer array 50, the backing material layer 54, and the like. In the example shown in FIGS. 3 and 4, the wiring board 60 on the ultrasonic transducer array 50 side is embedded in the backing material layer 54, and, in the backing material layer 54, the wiring board 60 is wired to the plurality of individual electrodes 52a of the electrode portion 52. The wiring board 60 has a plurality of electrode pads 62 for connecting the wiring board 60 to the plurality of individual electrodes 52a of the electrode portion 52, the wiring portion 64 that is disposed in a portion of the wiring board 60 on the lower side of the backing material layer 54 and that is composed of the plurality of connection portions 66 that are terminals that are electrically connected to the signal wires 56a of the plurality of coaxial cables 56, and the ground bar 68 that is at an end portion of the wiring board 60 on the lower side of the backing material layer 54 and that is electrically connected to the shield layers 56c (see FIGS. 4 and 5) of the plurality of coaxial cables 56. The plurality of electrode pads 62 and the plurality of connection portions 66 of the wiring portion 64 are electrically continuous with each other via wiring (not shown) or the like formed in the wiring board 60. In a case where, for example, the ground bar 68 is grounded and the transducer ground 52b of the electrode portion 52 is electrically connected to the ground bar 68, the plurality of electrode pads 62 may have terminals that are wired to the transducer ground 52b, and the transducer ground 52b and the ground bar 68 may be made electrically continuous with each other by using a lead wire or the like that passes along a side surface of the laminated body 47. As a matter of course, as a method for making the transducer ground 52b and the ground bar 68 electrically continuous with each other, a known method other than those described above may be used, as appropriate.

As means for electrically connecting the plurality of electrode pads 62 of the wiring board 60 and the plurality of individual electrodes 52a, known connection means, such as means for soldering signal wires and then filling and solidifying a backing material, may be used. With the structure in which the electrode pads 62 of the wiring board 60 are disposed in the backing material layer 54 in this way, wiring portions between the plurality of individual electrodes 52a and the plurality of electrode pads 62 are protected by the backing material layer 54, and therefore the probability of wire breakage at the wiring portions is reduced. The wiring board 60 need not be embedded in the backing material layer 54, provided that the wiring board 60 can electrically connect the electrode portion 52 and the signal wire 56a to each other. For example, in a case where the electrode portion 52 is disposed so as to extend to an end surface of the ultrasonic transducer array 50 in the width direction, the wiring board 60 may be disposed along the side surfaces of the ultrasonic transducer array 50 and the backing material layer 54 in the width direction (a side surface of the laminated body 47), that is, between the ultrasonic transducer array 50 and the backing material layer 54 and the copper foil 72. In this case, because wiring between the electrode portion 52 and the wiring board 60 can be performed after the backing material layer 54 has solidified, the operational efficiency when forming wiring is improved. In a case where, for example, the number of the plurality of ultrasonic transducers 48 (the number of channels of the ultrasonic transducer array 50) is large and it is difficult to provide, in the wiring board 60, a wiring space for connection with the plurality of coaxial cables 56, the number of wiring boards 60 may be increased as appropriate.

The insulating layer 70 of the ultrasonic transducer unit 46 is formed so as to be affixed along the side surfaces of the ultrasonic transducer array 50 and the backing material layer 54 in the width direction and extend to a side opposite to the ultrasonic transducer array 50 with respect to the backing material layer 54 (to the lower side of the backing material layer 54). In a case where the insulating layer 70 is not formed between the copper foil 72 and the ultrasonic transducer array 50 and the backing material layer 54, in particular, between the copper foil 72 and the connection portions 66 of the wiring board 60, the copper foil 72 and the connection portions 66 interfere with each other, and noise that the copper foil 72 receives from the outside is mixed into an observed ultrasonic echo signal (voltage signal). Accordingly, preferably, the insulating layer 70 is formed so as to cover the connection portions 66 of the wiring portion 64 of the wiring board 60 so that the copper foil 72 may not contact the connection portions 66. Therefore, as in the example shown in FIGS. 3 and 4, the insulating layer 70 may be removed at a portion where the ground bar 68 of the wiring portion 64 and the copper foil 72 are connected. The insulating layer 70 has a predetermined small thickness, because the insulating layer 70 is formed between the copper foil 72 and the ultrasonic transducer array 50 and the backing material layer 54. Preferably, the insulating layer 70 is made of an insulating material having heat conductivity, such as a heat conductive silicone sheet.

The copper foil 72 of the ultrasonic transducer unit 46 is affixed to side surface sides of the ultrasonic transducer array 50 and the backing material layer 54 in the width direction and on a side opposite to the backing material layer 54 with respect to the insulating layer 70. Moreover, the copper foil 72 is disposed on a side opposite to the ultrasonic transducer array 50 with respect to the backing material layer 54 so as to extend beyond the backing material layer 54, and is connected to the ground bar 68 of the wiring portion 64. The copper foil 72 receives heat generated from the plurality of ultrasonic transducers 48 of the ultrasonic transducer array 50 via the side surfaces of the ultrasonic transducer array 50 and the backing material layer 54 in the width direction of and the insulating layer 70, and dissipates the heat via the ground bar 68. Therefore, for example, a material having high heat conductivity, such as aluminum foil and a heat conductive silicone sheet, may be used instead of the copper foil 72. As connection means for connecting the copper foil 72 and the ground bar 68, any appropriate means can be used, provided that the means can electrically and thermally connect the copper foil 72 and the ground bar 68 while preventing heat damage to the plurality of ultrasonic transducers 48. Preferably, connection means that can be used at a temperature lower than a predetermined temperature may be used. Therefore, as connection means for connecting the copper foil 72 and the ground bar 68, a known method using a solder or a silver paste that does not require a predetermined amount of heat or more can be used.

Figure 7:
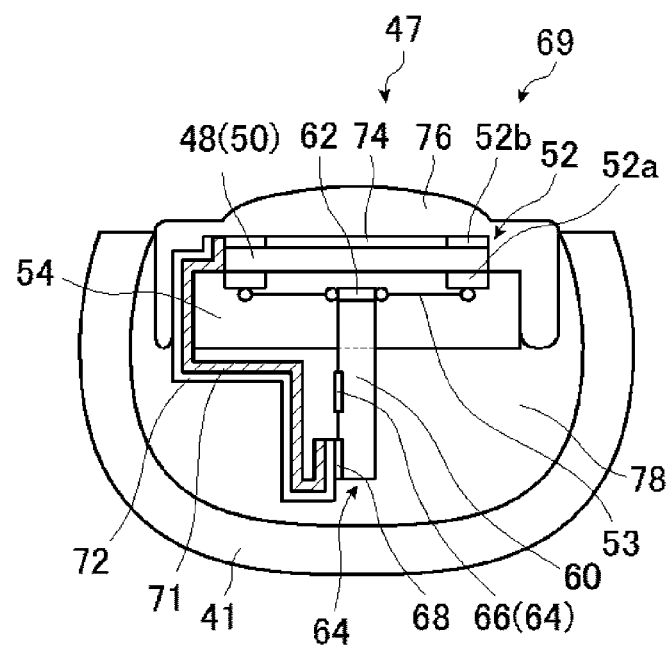
FIG. 7 is a cross-sectional view of another example of the ultrasonic transducer unit of the ultrasonic observation portion of the distal end portion of the ultrasonic endoscope shown in FIGS. 1 to 4.
Figure 8:
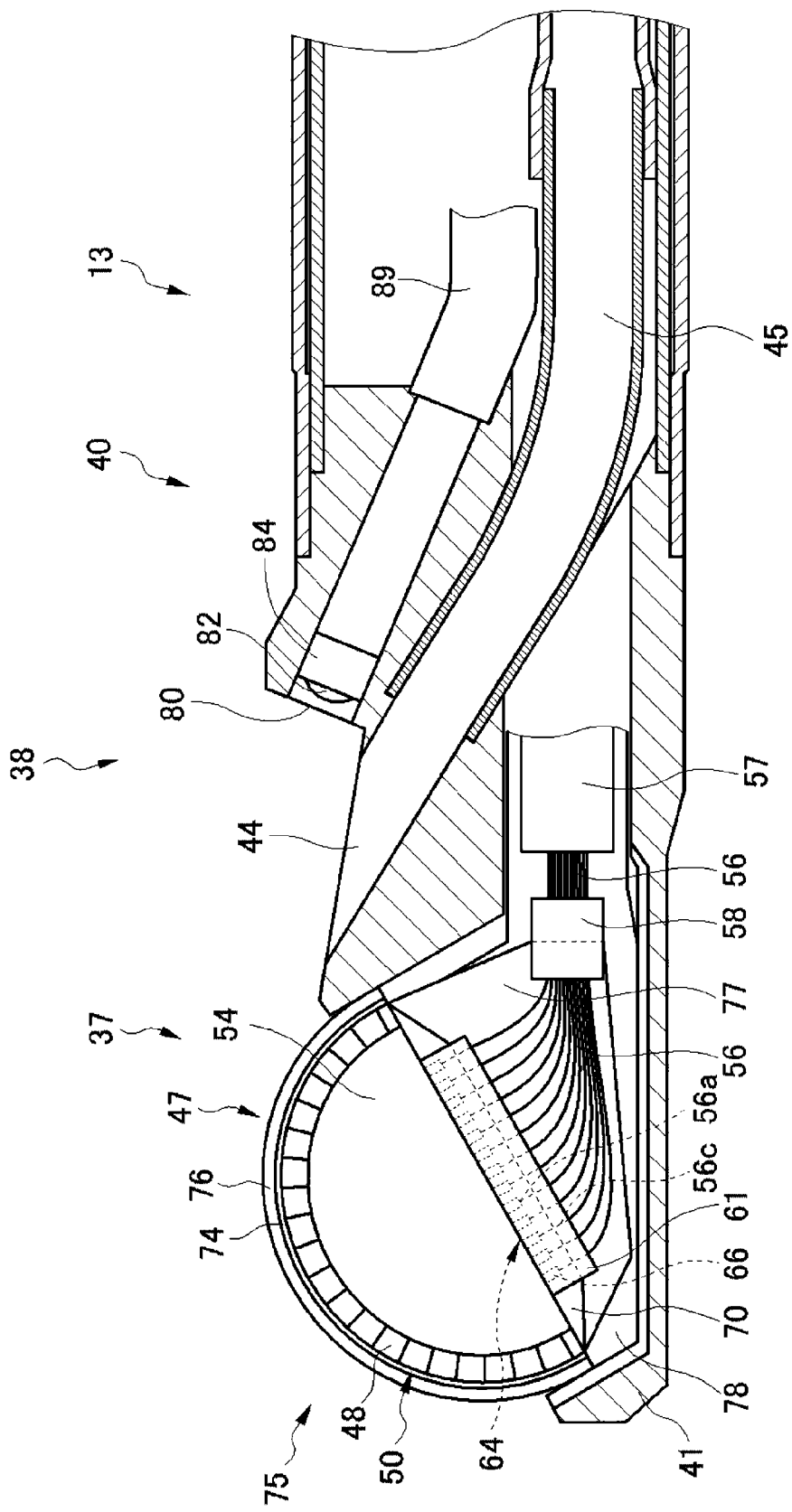
FIG. 8 is a longitudinal sectional view of an example of another ultrasonic transducer unit of the ultrasonic observation portion of the distal end portion of the ultrasonic endoscope shown in FIGS. 1 to 4.

As in the example shown in FIGS. 3 and 4, the copper foil 72 may be connected to the ground bar 68 of the wiring portion 64. However, as in another example of the present embodiment shown in FIG. 7, the copper foil 72 may be connected to the ground bar 68 by being folded back toward the side surface side of the ultrasonic transducer array 50 and the backing material layer 54 of an ultrasonic transducer unit 69 in the width direction. That is, the insulating layer 71 and the copper foil 72 are disposed so as to be folded back so that a surface of the copper foil 72 facing in a direction opposite to the ultrasonic transducer array 50 and the backing material layer 54 with respect to the insulating layer 71 is connected to the ground bar 68. By disposing the insulating layer 71 and the copper foil 72 in this way, it is not necessary to remove the insulating layer 71 on the way as in the example shown in FIGS. 3 and 4. Therefore, it is possible to reduce the number of steps for manufacturing the ultrasonic endoscope 12 and to improve the operational efficiency when performing wiring. Here, FIG. 7 is simplified for convenience of description as with FIG. 4, and the signal wires 56a of the coaxial cables 56 are omitted.

Here, in order to improve heat dissipation efficiency, the copper foils 72 may be disposed on both side surfaces of the ultrasonic transducer array 50 and the backing material layer 54 in the width direction (both side surfaces of the laminated body 47). In the case where, as illustrated in FIG. 4, only one wiring board 60 is provided, on a side opposite to a surface of the wiring board 60 on which the wiring portion 64 is disposed, only the copper foil 72 may be affixed to the side surfaces of the ultrasonic transducer array 50 and the backing material layer 54 in the width direction. For example, in a case where electrode portions 52 each of which is electrically continuous with a plurality of ultrasonic transducers 48 are disposed on both side surface sides of the ultrasonic transducer array 50 in the width direction or in a case where two or more wiring boards 60 are disposed, the insulating layers 70 and the copper foils 72 may be disposed on both side surface sides of the ultrasonic transducer array 50 and the backing material layer 54 in the width direction. In the case where the copper foils 72 are disposed on both side surface sides of the laminated body as described above, in order to improve heat dissipation efficiency, preferably, the copper foils 72 are connected to each other via a heat conductive member such as a copper foil 73, as in another example of the present embodiment shown in FIG. 6. In the example shown in FIG. 6, the copper foil 73, which is a heat conductive member, thermally connects the copper foil 72, which are disposed on both side surface sides of the laminated body 47, to each other through a side surface side of the wiring board 60 in the width direction by using a solder, a silver paste, or the like. Therefore, in particular, in a case where there is a difference between the numbers of the plurality of individual electrodes 52a of the electrode portion 52 (the number of channels of the ultrasonic transducer array 50) that are electrically continuous with the pair of wiring boards 60 to which the pair of copper foils 72 are thermally connected, it is possible to dissipate heat, which has been conducted to both copper foils 72, evenly to the shield layers 56c of the plurality of coaxial cables 56 (see FIGS. 3 and 5) via the ground bars 68 of the wiring boards 60. Also in the case where the number of wiring board 60 is one, compared with the case where the copper foil 72 is disposed on only one side surface of the laminated body 47, the number of heat conduction paths from the plurality of ultrasonic transducers 48 can be increased, and therefore heat dissipation efficiency is improved. The heat conductive member that thermally connects the copper foils 72 that are disposed on both side surface sides of the laminated body to each other may be any appropriate member that has high heat conductivity. Besides the copper foil 73, a known heat conductive member, such as aluminum or a heat conductive silicone sheet, can be used. Moreover, the shape of the heat conductive member is not limited to a foil shown in FIG. 6, and may be a plate-like shape or a wire-like shape.

Figure 6:
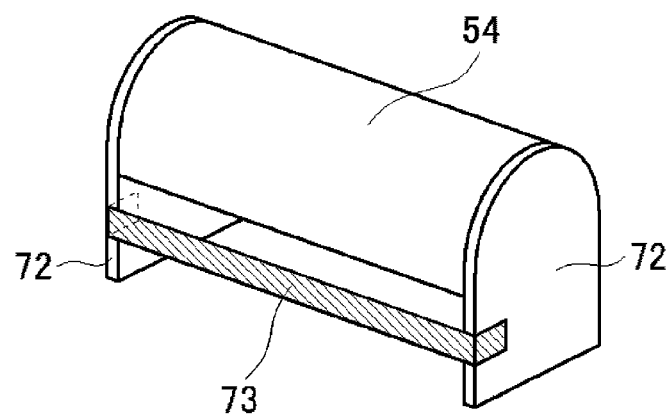
FIG. 6 is a schematic perspective view of another example of the ultrasonic transducer unit of the ultrasonic observation portion of the distal end portion of the ultrasonic endoscope shown in FIGS. 1 to 4.

FIG. 6 is a schematic view for illustrating a structure for thermally connecting the copper foils 72, which are disposed on body side surface sides of the laminated body, to each other by using the heat conductive member. In FIG. 6, only the backing material layer 54 is shown as the laminated body, and the wiring board 60, the insulating layer 70, and wiring in various portions such as the coaxial cables 56, are omitted.

As illustrated in FIGS. 3 and 4, the wiring portion 64 of the wiring board 60 is composed of the plurality of connection portions 66, which are electrically connected to the signal wires 56a of the plurality of coaxial cables 56. The wiring portion 64 is formed in a portion of the wiring board 60 on the lower side of the backing material layer 54. The plurality of connection portions 66 of the wiring portion 64 are each electrically continuous with a corresponding one of the plurality of electrode pads 62 of the wiring board 60 via wiring formed in or on the wiring board 60 or the like. Therefore, preferably, the number of the connection portions 66 of the wiring portion 64 is at least larger than or equal to the number of the plurality of ultrasonic transducers 48 that are electrically connected to the electrode pads 62 (the number of channels of the ultrasonic transducer array 50). In a case where, for example, the number of the plurality of ultrasonic transducers 48 is large, the wiring portion 64 may be composed of the plurality of connection portions 66 that are arranged in multiple rows. In the example shown in FIGS. 3 and 4, a surface of the wiring portion 64 on the copper foil 72 side is covered by the insulating layer 70 formed on the copper foil 72 so that the wiring portion 64 may not interfere with the copper foil 72, which is disposed on the side surface of the laminated body 47 in the width direction. In the case of electrically connecting the signal wires 56a of the coaxial cables 56 to the connection portions 66 and electrically connecting the shield layers 56c of the coaxial cables 56 to the ground bar 68, preferably, the wiring portion 64 is disposed on the same surface of the wiring board 60 as the ground bar 68 in the example shown in FIGS. 4 and 5. As a matter of course, the wiring portion 64 may be disposed at any appropriate position on the wiring board 60, provided that the operational efficiency when performing wiring is not impaired.

As illustrated in FIG. 3, the ground bar 68 of the wiring board 60 is an electroconductive member that is electrically connected to the shield layers 56c of the plurality of coaxial cables 56 and that is thermally connected to the copper foil 72 that is disposed along a side surface of the laminated body 47. Therefore, heat generated in the plurality of ultrasonic transducers 48 can be dissipated to the shield layers 56c of the plurality of coaxial cables 56 via the copper foil 72 and the ground bar 68. When thermally connecting the ground bar 68 and the copper foil 72, preferably, thermal connection means that can be used at a lower temperature, such as a low-temperature solder, a silver paste, or the like is used, in order to prevent heat damage to a portion where another member of the ground bar 68 and the copper foil 72 are thermally connected. For example, preferably, thermal connection means that can be used at a temperature lower than that of connection means used for connection portions between the ground bar 68, to which the copper foil 72 is thermally connected, and the shield layers 56c of the plurality of coaxial cables 56 is used. In a case where the ground bar 68 and the shield layers 56c of the plurality of coaxial cables 56 are thermally connected by using a solder, the ground bar 68 and the copper foil 72 may be connected to each other by using a solder having a lower melting point than the solder that is used to connect the ground bar 68 and the shield layers 56c of the plurality of coaxial cables 56.

Because the ground bar 68 is an electroconductive member, in a case where the shield layers 56c of the plurality of coaxial cables 56 are grounded, the ground potentials of the plurality of shield layers 56c, which are electrically connected to the ground bar 68, can be made to be the same potential, and, moreover, the copper foil 72, which is connected to the ground bar 68, can be grounded. In this case, because the copper foil 72 has a low potential, even when the copper foil 72 receives a noise (voltage signal), such as an electromagnetic wave from the outside, the copper foil 72 does not electromagnetically interfere with the plurality of ultrasonic transducers 48. Therefore, noise from the copper foil 72 can be prevented from being included in ultrasonic echo signals (voltage signals) of the plurality of ultrasonic transducers 48.

In the example illustrated FIGS. 3, 4, and 7, heat that is generated in the plurality of ultrasonic transducers 48 and conducted to the copper foil 72 is dissipated to the shield layers 56c of the plurality of coaxial cables 56 via the ground bar 68. A heat dissipation structure according to the present invention need not dissipate heat via the ground bar 68, provided that the heat dissipation structure can dissipate heat generated in the plurality of ultrasonic transducers 48 to the shield layers 56c of the plurality of coaxial cables 56. In another example of the present embodiment shown in FIG. 8, a wiring board 61 of an ultrasonic transducer unit 75 does not have the ground bar 68 shown in FIGS. 3, 4, and 7. Instead, an ultrasonic observation portion 37 has a collective ground portion 58 to which the shield layers 56c of the plurality of coaxial cables 56 are electrically connected.

As described above, the collective ground portion 58 is an electroconductive member to which the shield layers 56c of the plurality of coaxial cables 56 and a copper foil 77 (first heat conductive member) that is disposed along the side surfaces of the ultrasonic transducer array 50 and the backing material layer 54 in the width direction are electrically connected. The collective ground portion 58 is disposed on the plurality of coaxial cables 56 at a position on the proximal end side of an ultrasonic endoscope 13 relative to the wiring board 61. In the example shown in FIG. 8, the collective ground portion 58 is disposed on the plurality of coaxial cables 56 at a position between the wiring board 61 and the jacket 57. The outer jackets 56d of the plurality of coaxial cables 56 are removed at a portion where the coaxial cables 56 are electrically connected to the collective ground portion 58. Therefore, between the wiring board 61 and the collective ground portion 58, preferably, the coaxial cables 56 each have at least the signal wire 56a and the inner jacket 56b. The copper foil 77 is extended from the ultrasonic transducer array 50 and the backing material layer 54 beyond the wiring board 61 to the collective ground portion 58 and is thermally connected to the collective ground portion 58. Accordingly, heat generated in the plurality of ultrasonic transducers 48 is dissipated to the shield layers 56c of the plurality of coaxial cables 56 via the copper foil 77 and the collective ground portion 58. Also in a case where a plurality of wiring boards 61 are disposed, the method described above can be used. In this case, heat generated in the plurality of ultrasonic transducers 48 can be sufficiently dissipated to the shield layers 56c of all the coaxial cables 56 that are connected to the plurality of wiring boards 61.

Preferably, thermal connection means for thermally connecting the collective ground portion 58 and the copper foil 77 is means that uses a low temperature, such as a low-melting-point solder or a silver paste, as with the ground bar 68 of the wiring board 60 shown in FIGS. 3, 4, and 7. For example, in a case where the collective ground portion 58 and the shield layers 56c of the plurality of coaxial cables 56 are thermally connected to each other by using a solder, the collective ground portion 58 and the copper foil 77 may be connected by using a solder whose melting point is lower than that of a solder that is used to connect the collective ground portion 58 and the shield layers 56c of the plurality of coaxial cables 56.

Because the collective ground portion 58 is an electroconductive member, as with the ground bar 68 of the wiring board 60 shown in FIGS. 3, 4, and 7, in a case where the shield layers 56c of the plurality of coaxial cables 56 are grounded, the ground potentials of the plurality of shield layer 56c can be made to be the same potential. In this case, because the potential of the copper foil 77, which connected to the collective ground portion 58, can be made to be the ground potential, noise from the outside can be prevented from being included in ultrasonic echo signals (voltage signals) of the plurality of ultrasonic transducers 48.

With the structures of the ultrasonic observation portions 36 and 37 of the ultrasonic endoscopes 12 and 13 described above, heat generated from the plurality of ultrasonic transducers 48 of the ultrasonic transducer array 50 can be conducted to the copper foil 72 or 77, which is a heat conductive member; and the heat can be dissipated to the shield layers 56c of the plurality of coaxial cables 56 via the ground bar 68 or the collective ground portion 58. Moreover, because the connection portions 66 of the wiring portion 64, which are connected to the signal wires 56a of the plurality of coaxial cables 56, are covered by the insulating layer 70 or 71, the connection portions 66 and the copper foil 72 or 77 do not interfere with each other, and noise received from the outside can be prevented from being included in ultrasonic echo signals (voltage signals). Furthermore, each of the heat dissipation structures described above is a simple structure and does not occupy a large space in the distal end portion 40 of the ultrasonic endoscope 12 and 13. Accordingly, the heat dissipation structures can efficiently dissipate heat while maintaining the small size of the distal end portion 40 of the insertion portion 22. In the present embodiment, the heat dissipation structures of the convex-type ultrasonic endoscopes 12 and 13 have been described. However, the heat dissipation structures do not depend on the shape of the ultrasonic endoscope and, as a matter of course, can be used for an ultrasonic endoscope having another shape, such as a radial type.

As illustrated in FIGS. 2 and 3, the endoscopic observation portion 38 is composed of an observation window 80, an objective lens 82, a solid-state imaging element 84, illumination windows 86, a cleaning nozzle 88, a wiring cable 89 composed of coaxial cables and the like, and the like.

The observation window 80 is attached so as to be face diagonally upward from the distal end portion 40. Reflected light from an observation target site that has entered from the observation window 80 is focused by the objective lens 82 on an imaging surface of the solid-state imaging element 84. The solid-state imaging element 84 performs photoelectric conversion of the reflected light from the observation target site, which has passed through the observation window 80 and the objective lens 82 and has been focused on the imaging surface, and outputs a captured image signal. Examples of the solid-state imaging element 84 include a charge coupled device (CCD) and a complementary metal oxide semiconductor (CMOS). The captured image signal, which has been output from the solid-state imaging element 84, passes through the wiring cable 89, which extends from the insertion portion 22 to the operating unit 24, and is transmitted to the endoscope processor device 16 via the universal cord 26. The endoscope processor device 16 performs various types of signal processing and image processing on the transmitted captured image signal and displays an endoscopic optical image on the monitor 20.

The illumination windows 86 are disposed on both sides of the observation window 80. To each of the illumination windows 86, an emission end of a light guide (not shown) is connected. The light guide extends from the insertion portion 22 to the operating unit 24, and an input end thereof is connected to the light source device 18, which is connected via the universal cord 26. Illumination light that is emitted by the light source device 18 passes through the light guide emitted from the illumination window 86 toward observation target site.

In order to clean the surfaces of the observation window 80 and the illumination windows 86, the cleaning nozzle 88 ejects air or cleaning water toward the observation window 80 and the illumination windows 86 from the water supply tank 21a and the air/water supply pipe line in the ultrasonic endoscope 12.

The distal end portion 40 has the treatment tool lead-out port 44. The treatment tool lead-out port 44 is connected to a treatment tool channel 45 that is inserted into the insertion portion 22, and a treatment tool that is inserted into the treatment tool insertion port 30 is introduced from the treatment tool lead-out port 44 into a body cavity via the treatment tool channel 45. The treatment tool lead-out port 44 is located between the ultrasonic observation portion 36 and the endoscopic observation portion 38. In a case of forming a structure that allows a treatment tool that is introduced into a body cavity to be visually checked by using an ultrasonic image, preferably, the treatment tool lead-out port 44 is disposed near the ultrasonic observation portion 36.

Although not illustrated, a stand base that changes the lead-out direction of a treatment tool, which is introduced into a body cavity from the treatment tool lead-out port 44, may be disposed in the treatment tool lead-out port 44. A wire (not shown) is attached to the stand base, and, by operating a stand lever (not shown) of the operating unit 24 so as to push or pull the stand lever, the angle of the stand base changes, and thereby the treatment tool is lead out in a desired direction.

When observing the inside of a body cavity by using the ultrasonic endoscope 12, first, the insertion portion 22 is inserted into the body cavity, and an observation target site is searched while observing, on the monitor 20, an endoscopic optical image obtained by the endoscopic observation portion 38.

Next, when the distal end portion 40 reaches the observation target site and an instruction for obtaining an ultrasound tomographic image is given, a drive control signal is input from the ultrasonic processor device 14 to the ultrasonic transducers 48 via the signal wires 56a of the coaxial cables 56, the wiring board 60, and the electrode portion 52, which are disposed in the ultrasonic endoscope 12. When the drive control signal is input, predetermined voltages are applied to both electrodes of the ultrasonic transducers 48. Then, the piezoelectric bodies of the ultrasonic transducers 48 are excited, and ultrasound is emitted toward the observation target site via the acoustic lens 76.

After emitting the ultrasound, an echo signal from the observation target site is received by the ultrasonic transducers 48. Emission of the ultrasound and reception of the echo signal are repeatedly performed while sequentially switching among the ultrasonic transducers 48 that are driven by using an electronic switch such as a multiplexer. Thus, ultrasound is scanned over the observation target site. In the ultrasonic processor device 14, an ultrasound tomographic image is generated on the basis of a detection signal that is output from the ultrasonic transducers 48 after receiving the echo signal. The generated ultrasound tomographic image is displayed on the monitor 20.

Second Embodiment

In the first embodiment described with reference to FIGS. 1 to 8, a specific heat dissipation structure in a case where the number of the wiring board 60 is one has been mainly described. As described above, the number of wiring boards 60 need not be one. The number of wiring boards 60 may be increased, as appropriate, in a case where the number of channels of the ultrasonic transducer array 50 (the number of ultrasonic transducers 48) is large or in a case where the wiring space in the wiring board 60 is insufficient. Hereinafter, a case where a plurality of wiring boards are disposed in the ultrasonic transducer unit will be described. An ultrasonic transducer unit 246 according to the second embodiment shown in FIG. 9 differs from the ultrasonic transducer unit 46 according to the first embodiment, which is shown in FIG. 4, in the shapes of copper foils 272 (first heat conductive member), which are disposed on both side surface sides of the laminated body 47 and which are thermally connected to the plurality of ultrasonic transducers 48, and in that the ultrasonic transducer unit 246 has a plurality of flexible printed circuits 290a and 290b (hereinafter, simply referred to as the FPCs 290a and 290b). In other respects, the ultrasonic transducer units 46 and 246 have the same structure. Therefore, the same elements will be denoted by the same numerals, and detailed description will be omitted.

Figure 9:
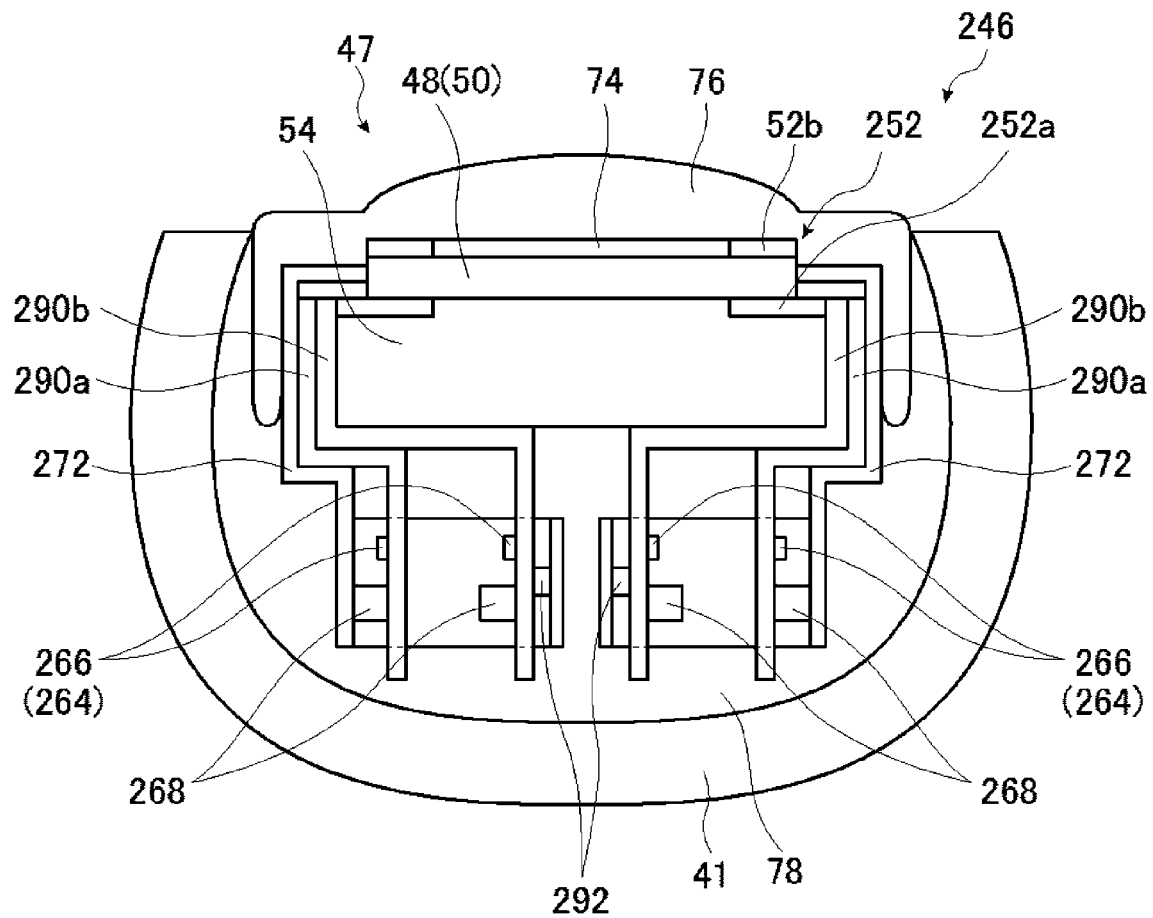
FIG. 9 is a cross-sectional view of an example of an ultrasonic transducer unit of an ultrasonic observation portion of a distal end portion of an ultrasonic endoscope according to a second embodiment of the present invention.

In the example shown in FIG. 9, the ultrasonic transducer unit 246 has an electrode portions 252 disposed on an outer surface of the ultrasonic transducer array 50, a pair of FPCs 290a each of which is electrically connected to a corresponding one of the electrode portions 252 at one end side thereof and is disposed on the outermost side with respect to the central side of the backing material layer 54, a pair of FPCs 290*b* (inner FPCs 290*b*) that are disposed between the pair of FPCs 290*a* and each of which is electrically connected to a corresponding one of the electrode portions 252 at one end side thereof, and a pair of copper foils 272 that are disposed along both side surfaces of the ultrasonic transducer array 50 and the backing material layer 54 in the width direction (side surfaces of the laminated body 47).

The numbers of the FPCs 290*a* and 290*b* that are disposed in the ultrasonic transducer unit 246 shown in FIG. 9 are not limited to those in the example shown in the figure and may be increased or decreased as appropriate in accordance with the number of the plurality of ultrasonic transducers 48 or the like. FIG. 9 is simplified for convenience of description, and an insulating layer (not shown) and a plurality of coaxial cables (not shown) are omitted. As a matter of course, in the ultrasonic transducer unit 246 according to the present embodiment shown in FIG. 9, as in the first embodiment shown in FIGS. 3, 4, and 7, an insulating layer may be formed on a surface of each of the copper foils 272 on the backing material layer 54 side (inner surface) so that the copper foil 272 and a wiring portion 264 (described below) of the FPC 290*a* do not interfere with each other.

As illustrated in FIG. 9, the electrode portions 252 of the ultrasonic transducer unit 246 are disposed in arc shapes on both end surface sides of the ultrasonic transducer array 50 (the ultrasonic transducers 48) (both end surface sides of the ultrasonic transducer array 50 in the width direction), which are perpendicular to the arc-shaped surface formed due to the arrangement of the plurality of ultrasonic transducers 48, that is, perpendicular to the longitudinal direction of the shapes of bar-shaped bodies of the ultrasonic transducers 48. The electrode portions 252 are each composed a plurality of individual electrodes 252*a* each of which is electrically continuous with a corresponding one of the plurality of ultrasonic transducers 48. In the present embodiment, the plurality of individual electrodes 252*a* are disposed on both end surface sides of the ultrasonic transducer array 50. However, if the number of ultrasonic transducers 48 is small, the individual electrodes 252*a* may be disposed only on one side. As in the first embodiment described above, the positions of the electrode portions 252 are not limited to the side surface sides of the ultrasonic transducer array 50 in the width direction, and may be on the central side of the ultrasonic transducer array 50 in the width direction.

Each of the outer FPC 290*a* of the ultrasonic transducer unit 246 is electrically connected to the individual electrodes 252*a* of the electrode portion 252, which is disposed on an end surface side of the ultrasonic transducer array 50 in the width direction, at one end thereof, and extends along the inner FPC 290*b*, which is disposed along a side surface of the laminated body 47, to the lower side of the backing material layer 54. In the example shown in FIG. 9, the outer FPC 290*a* has a plurality of electrode pads (not shown) for electrically connecting the FPC 290*a* to the plurality of individual electrodes 252*a* of the electrode portion 252; a wiring portion 264 that is disposed on a surface (outer surface) of the FPC 290*a* on a side opposite to the central side of the ultrasonic transducer unit 246 in a portion extending to the lower side of the backing material layer 54 and that is composed of a plurality of connection portions 266 that are electrically connected to signal wires (not shown) of the plurality of coaxial cables; and a ground bar 268 that is disposed on the same surface of the FPC 290*a* as the wiring portion 264 and that is electrically connected to shield layers (not shown) of a plurality of coaxial cables and thermally connected to the copper foil 272. Therefore, heat generated in the plurality of ultrasonic transducers 48 is dissipated to the shield layers of the plurality of coaxial cables via the copper foil 272 and the ground bar 268 of the FPC 290*a*.

In the example shown in the figures, the FPCs 290*a* and 290*b* are used as boards that is electrically connected to the electrode portion 252. However, the boards are not particularly limited to the FPCs 290*a* and 290*b*, provided that the boards can be electrically connected to the electrode portion 252 and can extend to the lower side of the backing material layer 54. For example, wiring boards made of a rigid material may be used, a part of each of the wiring boards may be embedded in the backing material layer 54 as with the wiring board 60 of the first embodiment shown in FIGS. 4 and 7, or each of the wiring boards may be disposed only on the lower side of the backing material layer 54.

As with the outer FPC 290*a*, each of the inner FPCs 290*b* of the ultrasonic transducer unit 246 is electrically connected to the individual electrodes 252*a* of the electrode portion 252, which is disposed on an end surface side of the ultrasonic transducer array 50 in the width direction, at one end thereof, and extends along a side surface of the laminated body 47 to the lower side of the backing material layer 54. In the example shown in FIG. 9, the inner FPC 290*b* has a plurality of electrode pads for electrically connecting the FPC 290*b* to the plurality of individual electrodes 252*a* of the electrode portion 252; a wiring portion 264 that is disposed on an outer surface of the FPC 290*b* in a portion extending to the lower side of the backing material layer 54 and that is composed of a plurality of connection portions 266 that are electrically connected to signal wires of the plurality of coaxial cables; a ground bar 268 that is disposed on the same surface of the FPC 290*b* as the wiring portion 264 and that is electrically connected to shield layers of the plurality of coaxial cables; and a ground pad 292 that is disposed on a surface (inner surface) of the FPC 290*b* on the central side of the ultrasonic transducer unit 246 and that is electrically continuous with the ground bar 268 via wiring formed in the FPC 290*b*. Moreover, the ground pad 292 is thermally connected to the copper foil 272. Therefore, heat generated in the plurality of ultrasonic transducers 48 is dissipated to the shield layers of the plurality of coaxial cables via the copper foil 272, the ground pad 292, the wiring in the FPC 290*b*, and the ground bar 268. The number of the inner FPCs 290*b* may be increased or decreased in accordance with the number of the plurality of ultrasonic transducers 48 and the like and is not limited to the number in the example shown in FIG. 9.

As with the copper foils 72 and 77 of the first embodiment shown in FIGS. 3, 4, and 6 to 8, each of the copper foils 272 of the ultrasonic transducer unit 246 is a member that is disposed along a side surface of the laminated body 47 and that conducts heat generated in the plurality of ultrasonic transducers 48. As described above, the copper foil 272 is disposed along the side surface of the laminated body 47 and extends to the lower side of the backing material layer 54. Moreover, the copper foil 272 has a shape that covers at least a part of side surfaces of the FPCs 290*a* and 290*b*. In the example shown in FIG. 10, the copper foil 272 has an inverted T-shape in a case where the backing material layer 54 is located on the upper side. On the back side of the backing material layer 54, a portion of the copper foil 272 extending toward an end portion of the ultrasonic transducer array 50 is bent a plurality of times in the same direction. In this way, in the example shown in FIG. 9, the copper foil 272 can be thermally connected to the ground bar 268 or the ground pad 292 by bending the portion of the copper foil 272 extending to the lower side of the backing material layer 54 so as to surround the wiring portions 264 of the FPCs 290a and 290b, the ground bar 268, and the ground pad 292. Therefore, in the example shown in the figures, by using the copper foil 272, the ground bar 268 of the outer FPC 290a and the ground pad 292 of the inner FPC 290b can be thermally connected to each other. Therefore, heat of the plurality of ultrasonic transducers 48 can be sufficiently dissipated to the shield layers of all coaxial cables that are connected to the FPCs 290a and 290b.

Figure 10:
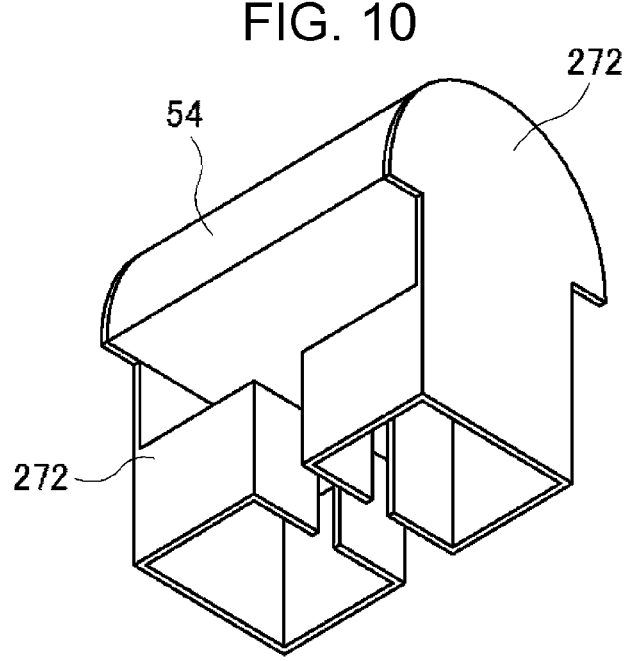
FIG. 10 is a schematic perspective view of the ultrasonic transducer unit of the ultrasonic observation portion shown in FIG. 9.

FIG. 10 is a schematic view of a structure in which the copper foil 272 is bent. In FIG. 10, among layers of the laminated body of the ultrasonic transducer unit 246, only the backing material layer 54 is illustrated, and wiring between portions such as the FPCs 290a and 290b, the coaxial cables, and the like are omitted.

As in the example of the first embodiment shown in FIG. 6, also in the example shown in FIG. 9, the pair of copper foils 272 that are disposed on both side surfaces of the laminated body 47 can be thermally connected to each other by using a heat conductive member (a third heat conductive member, not shown) such as a copper foil or a lead wire. In this case, for example, even if the total number of the FPCs 290a and 290b is an odd number and there is a difference in number between the FPCs 290b surrounded by two copper foils 272, heat of the plurality of ultrasonic transducers 48 conducted to the two copper foils 272 can be conducted to all shield layers (not shown) of coaxial cables (not shown) that are connected to the FPCs 290a and 290b. Therefore, difference between the amounts of heat conducted to the shield layers of the plurality of coaxial cables is eliminated, and therefore heat of the plurality of ultrasonic transducers 48 can be efficiently dissipated.

Preferably, connection means for thermally connecting the ground bar 268 and the ground pad 292 of the FPCs 290a and 290b to the copper foil 272 is connection means that uses low temperature, such as a low melting point solder or a silver paste. Moreover, preferably, the ground bar 268 and the ground pad 292 are thermally connected to the copper foil 272 by using thermal connection means that uses a temperature lower than that of connection means that is used in thermal connection portions where other members excluding the ground bar 268 and the ground pad 292 are connected to the copper foil 272. For example, when the ground bar 268 and a plurality of coaxial cables are connected by using a solder, the ground bar 268 and the ground pad 292 may be connected to the copper foil 272 by using a solder whose melting point is lower that of the solder that is used to connect the ground bar 268 and the plurality of coaxial cables.

As with the copper foils 72 and 77 of the first embodiment shown in FIGS. 3, 4, and 6 to 8, the copper foil 272 of the present embodiment shown in FIGS. 9 and 10 may be any appropriate member that can sufficiently conduct heat generated in the plurality of ultrasonic transducers 48. Therefore, instead of the copper foil 272, a member having high heat conductivity, such as an aluminum foil or a heat-conductive silicone sheet, may be used. Although not illustrated, in order to improve heat dissipation efficiency, preferably, the copper foil 272 is thermally connected, for example, to a shield layer (not shown) of a coaxial cable (not shown) or to a collective ground portion (not shown) that is thermally connected to shield layers of a plurality of coaxial cables. The shape of the copper foil 272 is not limited to the shape shown in FIGS. 9 and 10, and any appropriate shape may be used provided that the copper foil 272 can surround the plurality of FPCs 290a and 290b.

The wiring portions 264 of the FPCs 290a and 290b are each composed of the plurality of connection portions 266 that are terminals that are electrically connected to signal wires (not shown) of a plurality of coaxial cables. In the example shown in FIG. 9, the wiring portions 264 are disposed on the outer surfaces of the FPCs 290a and 290b. The plurality of connection portions 266 of the wiring portion 264 are electrically continuous with a plurality of electrode pads (not shown) of the FPCs 290a and 290b that are wired to the plurality of individual electrodes 52a via wiring (not shown) formed in the FPCs 290a and 290b. Preferably, the total number of the plurality of connection portions 266 of the wiring portion 264 is at least larger than or equal to the number of the plurality of electrode pads that are electrically continuous with the plurality of connection portions 266.

The ground bars 268 of the FPCs 290a and 290b are each a metal member that is electrically connected to the shield layers of the plurality of coaxial cables. In the example shown in FIG. 9, the ground bars 268 are disposed on the outer surfaces of the FPCs 290a and 290b. Preferably, as in the example shown in FIG. 9, the ground bars 268 are disposed on surfaces of the FPCs 290a and 290b on which the wiring portions 264 are disposed, because the signal wires of the plurality of coaxial cable are connected to the wiring portions 264 and the shield layers of the coaxial cables are connected to the ground bars 268 as described above. However, the positions of the ground bars 268 may be changed as appropriate in accordance with the wiring configuration. The wiring portions 264 and the ground bars 268 may be disposed on the inner surfaces of the FPCs 290a and 290b. The ground bars 268 may be disposed on the end surface sides of the FPCs 290a and 290b in the width direction (the end portion sides of the ultrasonic transducer array 50). In this case, the ground bar 268 can be thermally connected to the copper foils 272 on the end portion sides of the ultrasonic transducer array 50.

The ground pad 292 of the inner FPC 290b is an electro-conductive member that is electrically continuous with the ground bar 268, which is disposed on the outer surface of the FPC 290b, via wiring formed in the FPC 290b. In the example shown in FIG. 9, the ground pad 292 is disposed on the inner surface of the FPC 290b. In the example shown in the figures, the ground pad 292 is thermally connected to a bent portion of the copper foil 272 on the inner surface side of the FPC 290b. In the example shown in the figures, the ground pad 292 is disposed only on the inner FPC 290b. However, the ground pad 292 may be disposed on the outer FPC 290a, and, as with the ground bar 268 described above, the ground pads 292 may be disposed on the FPCs 290a and 290b on the end portion sides of the ultrasonic transducer array 50.

In FIGS. 9 and 10, it has been described that heat of a plurality of ultrasonic transducers 48 can be dissipated to the shield layers of the plurality of coaxial cables by thermally connecting the copper foil 272, which is bent so as to surround the FPCs 290a and 290b, to the ground bars 268 and the ground pads 292 of the FPCs 290a and 290b. Means for thermally connecting the ground bars 268 of the plurality of 290a and 290b to each other is not limited to the means described above. In another example of the present embodiment shown in FIG. 11, although a copper foil 295 of an ultrasonic transducer unit 294 is only thermally connected to the ground bar 268 of the outer FPC 290a, the ground bars 268 and the ground pads 292 of the FPCs 290a and 290b are connected by using copper plates 296a and 296b.

Figure 11:
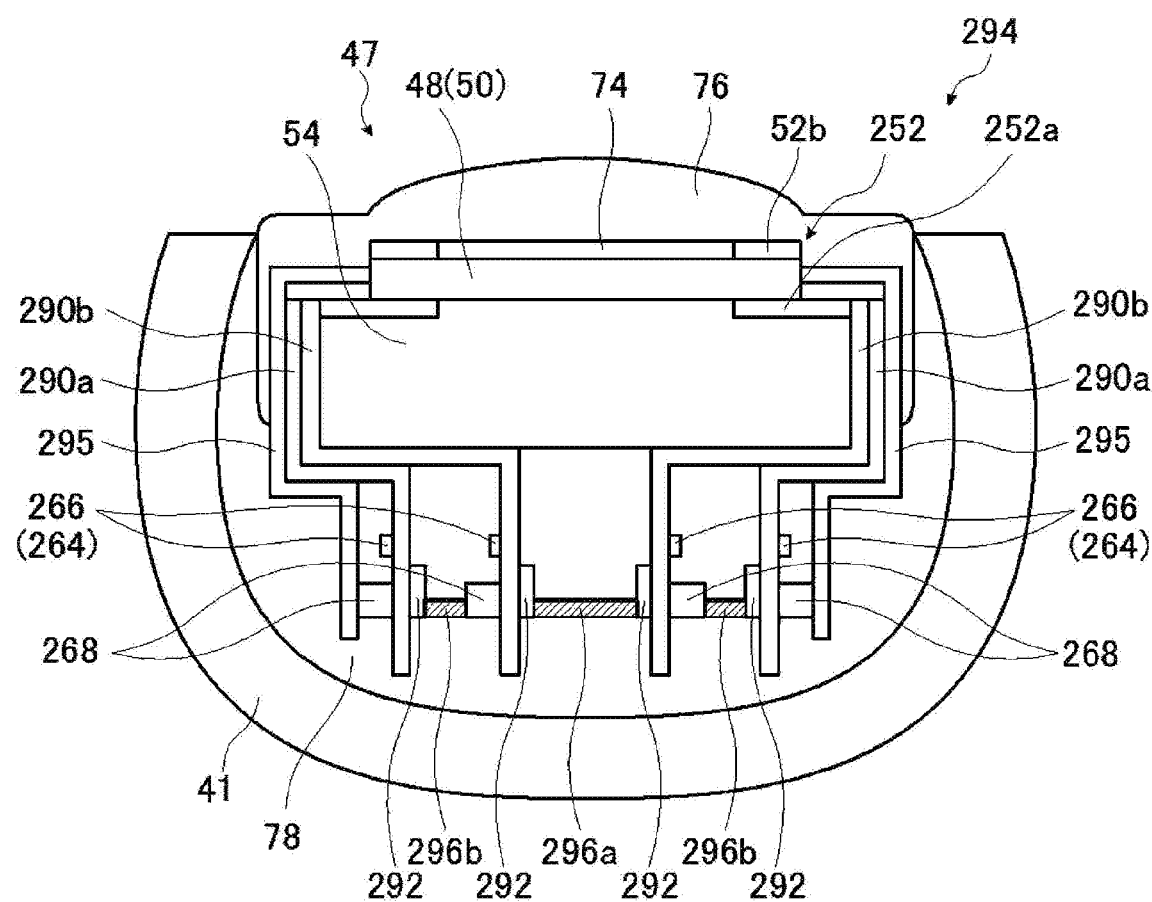
FIG. 11 is a cross-sectional view of another example of the ultrasonic transducer unit of the ultrasonic observation portion of the distal end portion of the ultrasonic endoscope shown in FIG. 9.

FIG. 11 is simplified for convenience of description as with FIG. 9, and a plurality of coaxial cables that are electrically connected to the FPCs 290a and 290b and insulating layers (not shown) formed on the inner surfaces of the copper foils 295 are omitted.

In the example shown in FIG. 11, the copper plate 296a (second heat conductive member) thermally connects the ground pads 292 that are disposed on the inner surfaces of the adjacent inner FPCs 290b. The copper plate 296b thermally connects the ground pad 292 disposed on the inner surface of the outer FPC 290a and the ground bar 268 disposed on the outer surface of the inner FPC 290b. Therefore, heat generated in the plurality of ultrasonic transducers 48 is conducted to the copper foil 295 disposed on a side surface of the laminated body 47, the ground bar 268 of the outer FPC 290a, wiring (not shown) formed in the outer FPC 290a, the ground pad 292 of the outer FPC 290a, the copper plate 296b, and the ground bar 268 of the inner FPC 290b. Moreover, the ground bars 268 of the adjacent FPCs 290a and 290b are thermally connected to each other via the FPCs 290a and 290b, the ground pads 292, and the copper plates 296a and 296b. Therefore, heat of the plurality of ultrasonic transducers 48 conducted to the copper foils 295 to both side surface sides of the laminated body 47 can be sufficiently dissipated to shield layers (not shown) of all coaxial cables (not shown) that are connected to the plurality of FPCs 290a and 290b, and heat dissipation efficiency can be improved.

Any other members may be used instead of the copper plate 296a and 296b, provided that the members are independent from the copper foil 295 and can thermally connect the ground bars 268 and the ground pads 292 of the adjacent FPCs 290a and 290b. For example, instead of the copper plate 296a or 296b, a solder wire, a lead wire having a larger diameter than the signal wire of the coaxial cable, an electroconductive mesh-like member, or the like can be used. As members that are used instead of the copper plate 296a and the copper plate 296b, members that are made of a metal having high thermal conductivity such as gold or silver, a heat conductive ceramic, a heat conductive silicone, or the like can be used.

With the second embodiment of the present invention described above, by thermally connecting the plurality of ground bars 268 of the FPCs 290a and 290b of the ultrasonic transducer units 246 and 294 to each other, heat of the plurality of ultrasonic transducers 48 can be sufficiently dissipated to the shield layers of all coaxial cables that are connected to the plurality of FPCs 290a and 290b. As in the first embodiment illustrated FIGS. 1 to 8, also in the present embodiment, a heat dissipation structure of a convex-type ultrasonic endoscope has been described. However, as a matter of course, the heat dissipation structure does not depend on the shape of the ultrasonic endoscope and can be used for an ultrasonic endoscope having another shape such as a radial type.

Third Embodiment

Figure 12:
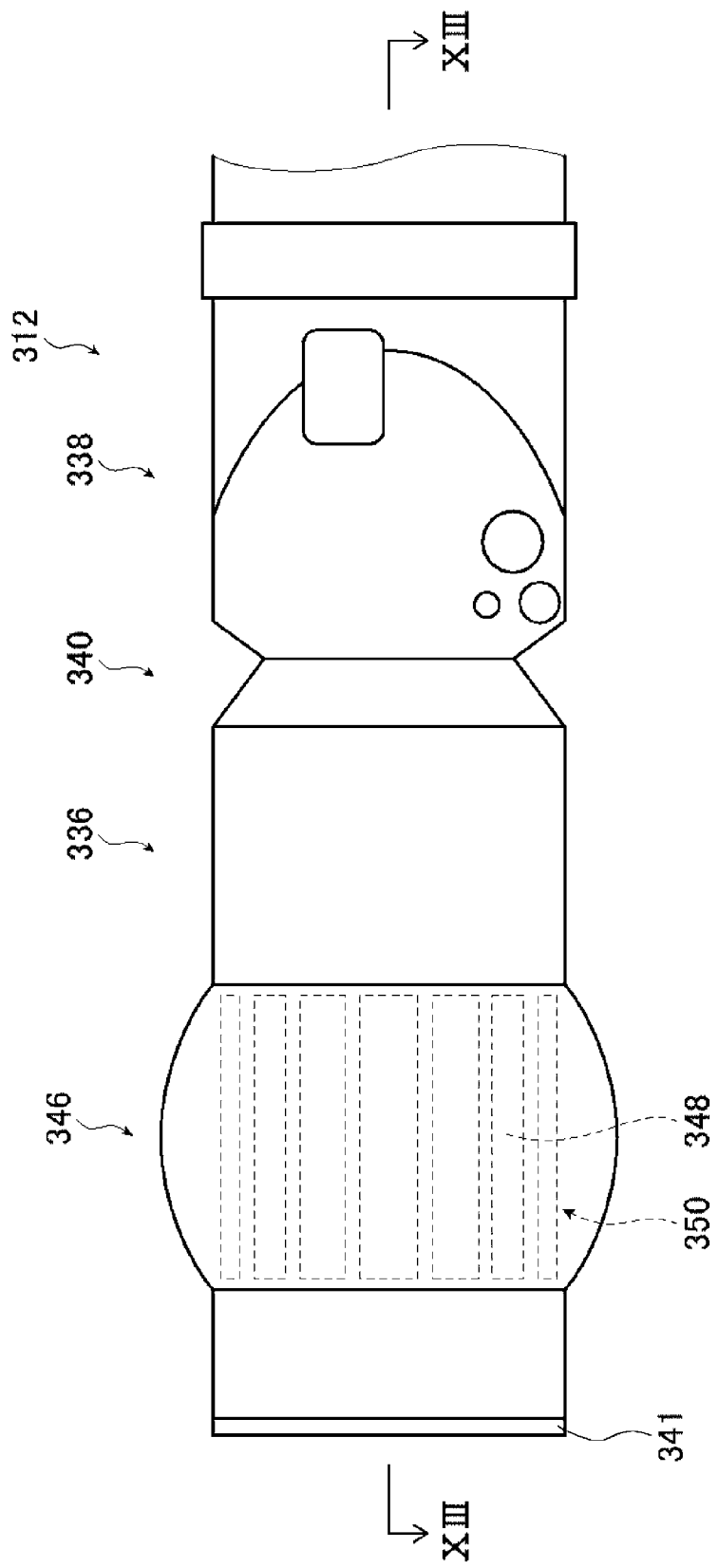
FIG. 12 is a partial enlarged plan view of a distal end portion of an ultrasonic endoscope according to a third embodiment of the present invention.
Figure 13:
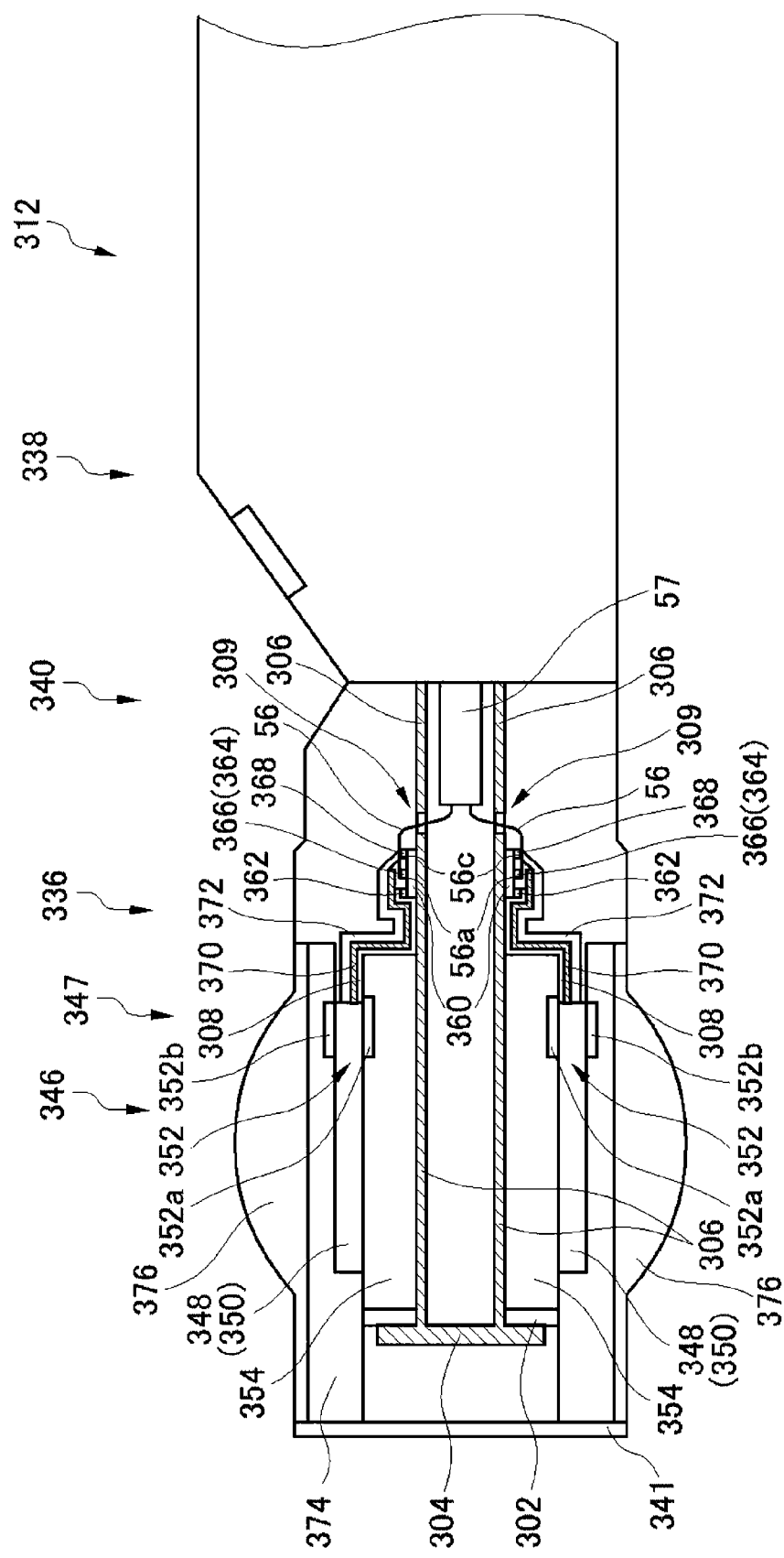
FIG. 13 is a partial longitudinal sectional view taken along line XIII-XIII in FIG. 12, illustrating the distal end portion of the ultrasonic endoscope shown in FIG. 12.

Heretofore, cases where a heat dissipation structure according to the present invention is mainly applied to a convex-type ultrasonic endoscope have been described. However, a heat dissipation structure according to the present invention can be also applied to an ultrasonic endoscope having an ultrasonic observation portion of a type other than the convex type, such as a radial type. In the present embodiment, a heat dissipation structure of a radial-type ultrasonic observation portion will be described. An ultrasonic endoscope 312 according to the present embodiment shown in FIGS. 12 and 13 differs from the ultrasonic endoscope 12 according to the first embodiment shown in FIGS. 1 to 3 in that the ultrasonic endoscope 312 includes a distal end portion 340 that includes a radial-type ultrasonic observation portion 336 and an endoscopic observation portion 338, instead of the distal end portion 40 that includes the convex-type ultrasonic observation portion 36 and the endoscopic observation portion 38. In other respects, the ultrasonic endoscope 312 has the same structure as the ultrasonic endoscope 12. In the radial-type ultrasonic observation portion 336, in particular, members that are the same as the coaxial cables 56 and the jacket 57 of the first embodiment shown in FIGS. 3 and 5 are used. In FIGS. 12 and 13, the coaxial cables 56 and the jacket 57 are denoted by the same numerals as in FIGS. 3 and 5, and detailed description will be omitted.

FIG. 12 is a partial enlarged plan view of a distal end portion of an insertion portion of an ultrasonic endoscope according to the present embodiment. FIG. 13 is a partial longitudinal sectional view taken along line XIII-XIII in FIG. 12, illustrating the distal end portion of the insertion portion of the ultrasonic endoscope shown in FIG. 12.

As illustrated in FIGS. 12 and 13, the ultrasonic endoscope 312 according to the present embodiment is a radial-type ultrasonic endoscope that includes an ultrasonic transducer unit 346 in the ultrasonic observation portion 336 of the distal end portion 340. The ultrasonic transducer unit 346 includes an ultrasonic transducer array 350 in which a plurality of ultrasonic transducers 348 are cylindrically arranged. In the example shown in FIGS. 12 and 13, the ultrasonic observation portion 336 is disposed on the distal end side of the ultrasonic endoscope 312 relative to the endoscopic observation portion 338.

As with the ultrasonic endoscopes 12 and 13 of the first embodiment shown in FIGS. 1 to 3, the ultrasonic endoscope 312 according to the present invention may include a mechanism for leading out treatment tools, such as forceps, a puncture needle, and a high-frequency knife. A treatment tool lead-out port (not shown), from which these treatment tools are led out, may be formed on the distal end side or on the proximal end side of the ultrasonic endoscope 312 relative to the plurality of ultrasonic transducers 348.

The endoscopic observation portion 338 of the ultrasonic endoscope 312 according to the present embodiment has a structure similar to that of the endoscopic observation portion 38 of the ultrasonic endoscope 12 of the first embodiment shown in FIGS. 2 and 3. As a matter of course, the endoscopic observation portion 338 has an observation window (80), an objective lens (82), a solid-state imaging element (84), an illumination window (86), a cleaning nozzle (88), a wiring cable (89), and the like.

As illustrated in FIGS. 12 and 13, the ultrasonic observation portion 336 according to the present embodiment is composed of the ultrasonic transducer unit 346, an exterior member 341 for attaching and holding the ultrasonic transducer unit 346, the plurality of coaxial cables 56 that are wired to the ultrasonic transducer unit 346 and whose proximal end sides are bundled together in the jacket 57.

In the example shown in FIG. 13, the ultrasonic transducer unit 346 has the ultrasonic transducer array 350 in which the plurality of ultrasonic transducers 348 are cylindrically arranged, an electrode portion 352 that is electrically continuous with the ultrasonic transducer array 350, a backing material layer 354 that supports the ultrasonic transducers 348 of the ultrasonic transducer array 350 from a side of a surface on the central side of the ultrasonic transducer unit 346 (inner surfaces of the ultrasonic transducer 348), an acoustic matching layer 374 that is laminated on a side opposite to the backing material layer 354 with respect to the ultrasonic transducer array 350 (outer side of the ultrasonic transducer array 350), and an acoustic lens 376 that is laminated on a side opposite to the ultrasonic transducer array 350 with respect to the acoustic matching layer 374 (outer side of the acoustic matching layer 374). As described above, the ultrasonic transducer unit 346 has a laminated body 347 that is composed of the acoustic lens 376, the acoustic matching layer 374, the ultrasonic transducer array 350, and the backing material layer 354.

The ultrasonic transducers 348, the ultrasonic transducer array 350, the electrode portion 352, the backing material layer 354, the acoustic matching layer 374, an acoustic lens 378, and the laminated body 347 according to the present embodiment differ in shape but do not differ in structure and function from the ultrasonic transducers 48, the ultrasonic transducer array 50, the electrode portion 52, the backing material layer 54, the acoustic matching layer 74, the acoustic lens 76, and the laminated body 47 of the first embodiment shown in FIGS. 2 to 4. Therefore, description of these elements will be omitted.

The ultrasonic transducer unit 346 has an annular plate 302 that is disposed in such a way that a side surface thereof on the distal end side of the ultrasonic endoscope 312 contacts a side surface of the backing material layer 354 on the distal end side of the ultrasonic endoscope 312 and that fixes the position of a cylindrical member 306 (described below); a support plate 304 that is joined to a surface of the annular plate 302 on a side opposite to the backing material layer 354 and that is a disk-shaped plate having an outside diameter larger than the inside diameter of the annular plate 302; the cylindrical member 306 that contacts a surface of the backing material layer 354 on a side opposite to the ultrasonic transducer array 350 (inside of the backing material layer 354), that is joined to the support plate 304 at an end surface thereof on the distal end side of the ultrasonic endoscope 312, and that supports the laminated body 347; a wiring board 360 that is disposed on an outer peripheral portion of the cylindrical member 306 on the proximal end side of the ultrasonic endoscope 312 relative to the backing material layer 354 and that is electrically connected to the plurality of coaxial cables 56 and the electrode portion 352; a copper foil 372 that is disposed along the side surfaces of the plurality of ultrasonic transducers 48 and the backing material layer 354 on the proximal end side of the ultrasonic endoscope 312 and that is thermally connected to a ground bar 368 (described below) disposed in the wiring board 360; and an insulating layer 370 that is formed on a surface of the copper foil 372 on the backing material layer 354 side (inner surface of the copper foil 372). The electrode portion 352 and the wiring board 360 are electrically connected to each other by using a wiring cable 308 or the like.

The electrode portion 352 of the ultrasonic transducer unit 346 has individual electrodes 352a for transmitting and receiving voltage signals, such as drive signals and ultrasonic echo signals, to and from the plurality of ultrasonic transducers 348, and a transducer ground 352b that is a ground electrode for the plurality of ultrasonic transducers 348. In the example shown in FIG. 13, each of the individual electrodes 352a is disposed at an end portion of the ultrasonic transducer 348 on an inner side and on the proximal end side of the ultrasonic transducer 348, and is electrically connected to a plurality of electrode pads 362 (described below) of the wiring board 360. Although not illustrated, the transducer ground 352b is electrically connected to a grounded portion in the ultrasonic endoscope 312 by using a lead wire or the like. As described below, because the plurality of electrode pads 362, which are electrically connected to the plurality of individual electrodes 352a of the electrode portion 352, are electrically continuous with the signal wires 56a of the plurality of coaxial cables 56, the plurality of individual electrodes 352a of the electrode portion 352 are electrically continuous with the signal wires 56a of the coaxial cables 56.

Because the transducer ground 352b is a ground electrode for the plurality of ultrasonic transducers 348, preferably, the ground potentials thereof are the same potential. Therefore, preferably, the transducer ground 352b is a common electrode for the plurality of ultrasonic transducers 348. Moreover, provided that the transducer ground 352b can be electrically connected to a grounded portion, the transducer ground 352b need not be grounded via the electrode pads 362 of the wiring board 360, and need not be electrically continuous with the shield layers 56c of the plurality of coaxial cables 56. For example, the transducer ground 352b and the ground bar 368 may be electrically connected to each other via a lead wire or the like that is independent from the wiring board 360. Alternatively, the transducer ground 352b and a grounded portion in the ultrasonic endoscope 312 may be electrically connected to each other by using a lead wire or the like. The positions of the plurality of individual electrodes 352a and the transducer ground 352b are not limited to those shown in FIG. 11, provided that the individual electrodes 352a and the transducer ground 352b can be connected to the signal wires 56a and the grounded portion. That is, the positions may be on parts of the ultrasonic transducer 348 on the distal end side of the ultrasonic endoscope 312, or over the entirety of the inner surface and the outer surface of the ultrasonic transducer 348; or the positions may be changed as appropriate in accordance with the structure of the ultrasonic observation portion 336.

As illustrated in FIG. 13, the wiring board 360 of the ultrasonic transducer unit 346 is disposed on an outer peripheral portion of the cylindrical member 306 on the proximal end side of the backing material layer 354 and is electrically connected to the electrode portion 352. The wiring board 360 has the plurality of electrode pads 362 that are disposed in a portion thereof on the distal end side of the ultrasonic endoscope 312 (distal end side of the wiring board 360), a wiring portion 364 that is disposed in a portion thereof on the proximal end side of the wiring board 360 relative to the plurality of electrode pads 362, and the ground bar 368 that is disposed in a portion of the wiring board 360 on the most proximal end side. The plurality of electrode pads 362 are members that are to be connected to the plurality of individual electrodes 352a of the electrode portion 352. The wiring portion 364 is composed of a plurality of connection portions 366 that are terminals that are electrically continuous with the plurality of electrode pads 362 via wiring (not shown) formed in the wiring board 360 and that are electrically connected to the signal wires 56a of the plurality of coaxial cables 56. The ground bar 368 is electrically connected to the shield layers 56c of the plurality of coaxial cables 56.

The wiring board 360 may be any appropriate member that can electrically connect the plurality of individual electrodes 352a of the electrode portion 352 and the signal wires 56a of the plurality of coaxial cables 56. An FPC may be used as the wiring board 360, or the wiring board 360 may have a cylindrical shape that surrounds the cylindrical member 306. In a case where, for example, the number of the plurality of ultrasonic transducers 348 (the number of channels the ultrasonic transducer array 350) is large, a plurality of the wiring boards 360 may be disposed, and the wiring boards 360 may be arranged side by side so as to surround the cylindrical member 306.

The copper foil 372 of the ultrasonic transducer unit 346 conducts heat that is generated in the plurality of ultrasonic transducers 348. The copper foil 372 is disposed along the side surfaces of the plurality of ultrasonic transducers 348 and the backing material layer 354 on the proximal end side and is thermally connected to the ground bar 368 of the wiring board 360. The ground bar 368 of the wiring board 360 is electrically connected, that is, thermally connected, to the shield layers 56c of the plurality of coaxial cables 56. Therefore, the ground bar 368 can dissipate heat of the plurality of ultrasonic transducers 48 to the shield layers 56c of the plurality of coaxial cables 56 via the copper foil 372. As with the copper foils 72, 77, and 272 shown in FIGS. 3, 4, and 6 to 11, instead of the copper foil 372, a heat conductive member made of a metal having high heat conductivity, such as aluminum, gold, or silver, or a heat conductive silicone may be used. Moreover, instead of a foil shape, a known structure having flexibility, such as a mesh shape and a sheet shape, may be used.

As illustrated in FIG. 13, as with the insulating layer 70 of the first embodiment shown in FIG. 4, the insulating layer 370 of the ultrasonic transducer unit 346 is formed on a surface of the copper foil 372 on the backing material layer 354 side (inner surface of the backing material layer 354). In order to prevent interference between the plurality of connection portions 366, to which the signal wires 56a of the plurality of coaxial cables 56 are electrically connected, and the copper foil 372, the insulating layer 370 is removed at least at a portion where the copper foil 372 is connected to the ground bar 368 of the wiring board 360. Therefore, the copper foil 372, the signal wires 56a of the plurality of coaxial cables 56, and the plurality of individual electrodes 352a of the electrode portion 352 do not interfere with each other, and noise (voltage signal) that the copper foil 372 receives from the outside can be prevented from being included in ultrasonic echo signals (voltage signals) that the plurality of ultrasonic transducers 348 transmit and receive.

A connection method of thermally connecting the copper foil 372 and the insulating layer 370 of the ultrasonic transducer unit 346 to the ground bar 368 of the wiring board 360 is not limited to the example shown in FIG. 13. In another example of the present embodiment shown in FIG. 14, an insulating layer 371 is formed on the entirety of the inner surface of the copper foil 372. Moreover, the copper foil 372 is folded back, at an end portion thereof on a side opposite to an end portion that is thermally connected to the laminated body 347 (distal end portion of the copper foil 372), so that the outer surface of the copper foil 372 faces the central side of an ultrasonic transducer unit 369. Then, the end portion of the copper foil 372 contacts the ground bar 368 of the wiring board 360 and is thermally connected to the ground bar 368. At this time, as in the example shown in FIG. 14, the wiring portion 364 of the wiring board 360 is covered by the insulating layer 371 and does not interfere with the copper foil 372.

Figure 14:
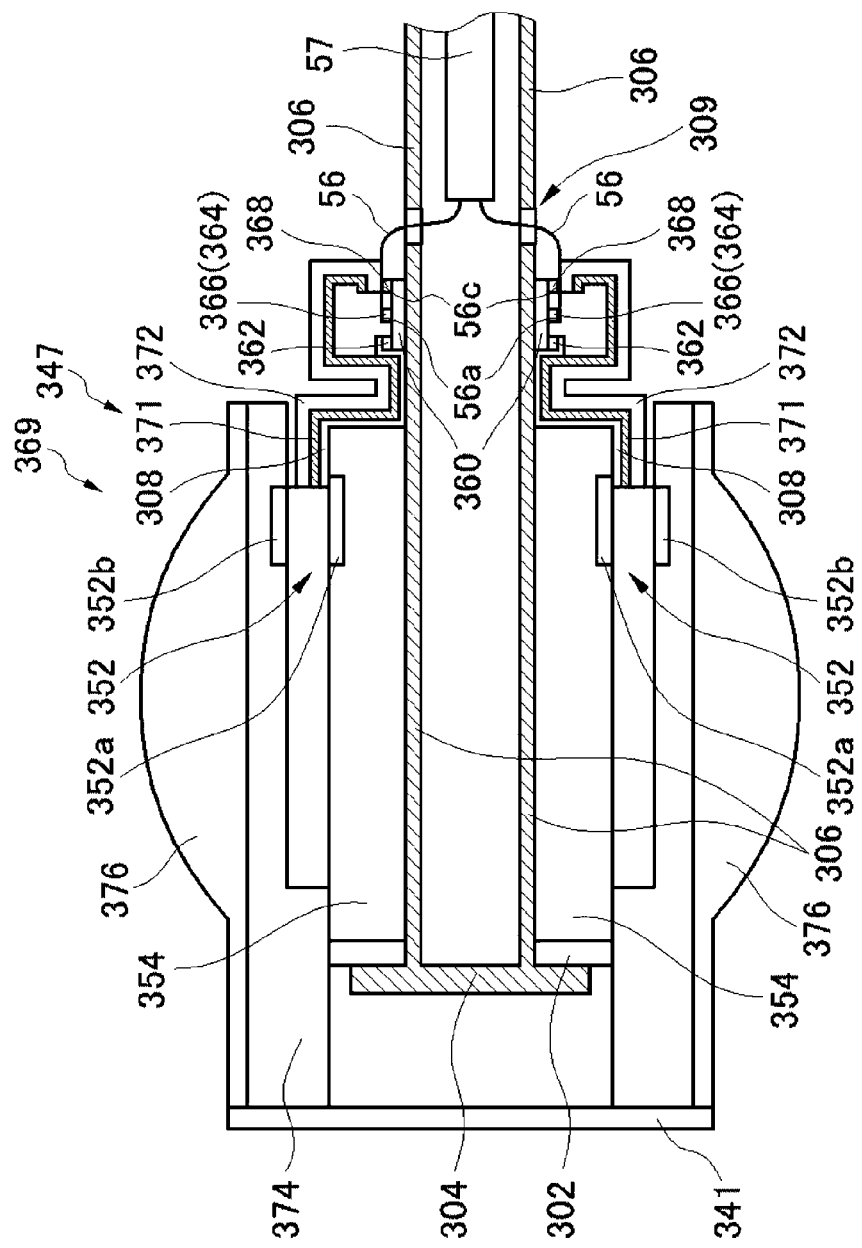
FIG. 14 is a partial longitudinal sectional view of another example of the ultrasonic transducer unit shown in FIG. 13.
Figure 15:
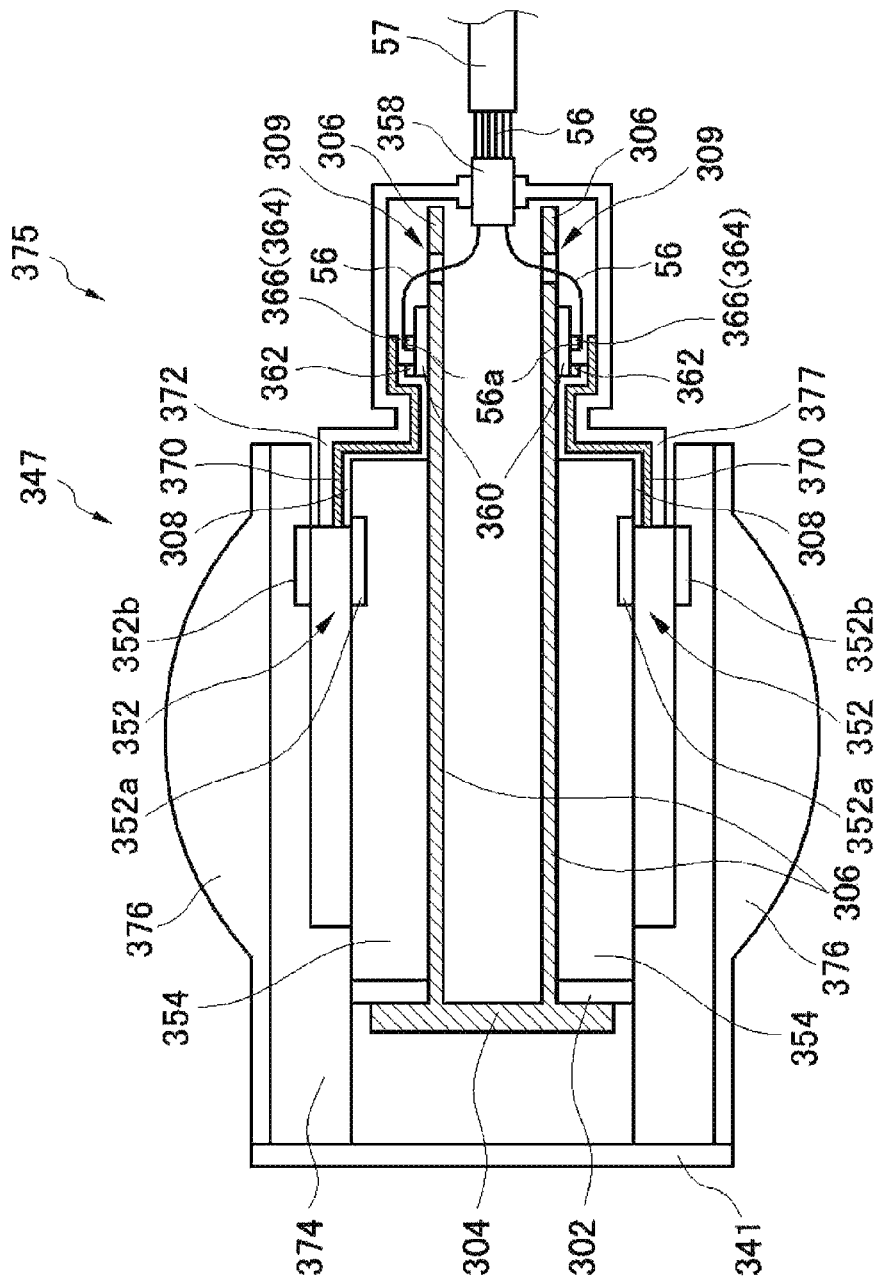
FIG. 15 is a partial longitudinal sectional view of another example of the ultrasonic transducer unit shown in FIGS. 13 and 14.

In the examples shown in FIGS. 13 and 14, heat generated in the plurality of ultrasonic transducers 348 can be dissipated to the shield layers 56c of the plurality of coaxial cables 56 via the copper foil 372 and the ground bar 368 of the wiring board 360. Moreover, by forming the insulating layer 370 and 371 on the copper foil 372, interference between the copper foil 372 and the wiring portion 364 of the wiring board 360 can be prevented. As described above, the ground bar 368 is used in the heat dissipation structure according to the present embodiment. However, a member other than the ground bar 368 may be used, provided that the member can dissipate heat of the plurality of ultrasonic transducers 348 to the shield layers 56c of the plurality of coaxial cables 56. In another example of the present embodiment shown in FIG. 15, an ultrasonic transducer unit 375 does not have the ground bar 368 shown in FIGS. 13 and 14, and has an electroconductive collective ground portion 358, to which the shield layers 56c of the plurality of coaxial cables 56 are electrically connected, on the proximal end side relative to the wiring board 360. Moreover, a copper foil 377, which is disposed along the side surfaces of the plurality of ultrasonic transducers 348 and the backing material layer 354 on the proximal end side, is extended to the collective ground portion 358 and is thermally connected to the collective ground portion 358. Therefore, with the structure of the example shown in FIG. 15, heat of the plurality of ultrasonic transducers 348 can be dissipated to the shield layers 56c of the plurality of coaxial cables 56 via the copper foil 377 and the collective ground portion 358. As illustrated in FIG. 13, the support plate 304 of the ultrasonic transducer unit 346 is a disk-shaped plate that is disposed in contact with a surface of the annular plate 302 on a side opposite to the backing material layer 354 and that has an outside diameter larger than the inside diameter of the annular plate 302. The support plate 304 fixes the positions of the annular plate 302 and the cylindrical member 306. Therefore, in order to fix the position of the cylindrical member 306, preferably, the support plate 304 is joined to the cylindrical member 306, or may be a member that is integrated with the cylindrical member 306. Moreover, in a case where the support plate 304 is joined to the cylindrical member 306, in order to fix the position of the cylindrical member 306, preferably, the support plate 304 is joined also to the annular plate 302. The shape of the support plate 304 is not limited to a disk-like shape and may be any appropriate shape, such as a polygonal shape, provided that the support plate 304 can fix the positions of the annular plate 302 and the cylindrical member 306.

The cylindrical member 306 of the ultrasonic transducer unit 346 is disposed in contact with the inner surface of the backing material layer 354, the inner surface of the annular plate 302, and a surface of the support plate 304 on a side opposite to the distal end side of the ultrasonic endoscope, and fixes the laminated body 347. The plurality of coaxial cables 56, which are covered by the jacket 57, are disposed in a space in the cylindrical member 306 on the central side of the ultrasonic transducer unit 346 (inside of the cylindrical member 306). Moreover, a plurality of slits 309, for leading out the plurality of coaxial cables 56 toward the outer peripheral side of the cylindrical member 306, are formed in a portion of the cylindrical member 306 on the proximal end side of the backing material layer 354. The cylindrical member 306 may be made of any appropriate material such as a metal or a resin, provided that the cylindrical member 306 can support the laminated body 347.

As illustrated in FIG. 13, the plurality of electrode pads 362 of the wiring board 360 are disposed on the distal end side of the wiring board 360 and are electrically connected to the plurality of individual electrodes 352a of the electrode portion 352 by using the wiring cable 308 or the like. The plurality of electrode pads 362 are each electrically continuous with a corresponding one of the plurality of connection portions 366 of the wiring portion 364 via wiring (not shown) formed in the wiring board 360. In the ultrasonic transducer unit 346, even in a case where a plurality of the wiring boards 360 are disposed, if a large number of electrode pads 362 are disposed because, for example, the number of channels the ultrasonic transducer array 350 is large, the electrode pads 362 may be arranged in multiple rows. Wiring means for wiring the plurality of electrode pads 362 and the plurality of individual electrodes 352a is not limited to the wiring cable 308 illustrated in the figures. Known wiring means, such as lead wires or a FPC, may be used, provided that the wiring means can electrically connect the plurality of electrode pads 362 and the plurality of individual electrodes 352a.

The wiring portion 364 of the wiring board 360 is composed of the plurality of connection portions 366, which are terminals each of which is wired to a corresponding one of the signal wires 56a of the plurality of coaxial cables 56. In the example shown in FIG. 13, the wiring portion 364 is disposed between the plurality of electrode pads 362 and the ground bar 368 of the wiring board 360. Preferably, the total number of the plurality of connection portions 366 of the wiring portion 364 is at least larger than or equal to the total number of the plurality of electrode pads 362 of the wiring board 360. In a case where, for example, the number of channels the ultrasonic transducer array 350 is large, as with the plurality of electrode pads 362, the connection portions 366 may be arranged in multiple rows. Although not illustrated, preferably, wiring portions between the signal wires 56a of the plurality of coaxial cables 56 and the plurality of connection portions 366 of the wiring portion 364 are covered by a filler (not shown) made of an insulating resin or the like, in order to prevent wire breakage at the wiring portions.

Heretofore, ultrasonic endoscopes each having a heat dissipation structure according to the present invention have been described. However, the present invention is not limited to the examples described above, and, as a matter of course, may be improved or modified in various ways within the spirit and scope of the present invention. As a matter of course, the embodiments and the plurality of examples described above may be used in combination as appropriate.

REFERENCE SIGNS LIST 10 ultrasonic inspection system
12, 13, 312 ultrasonic endoscope
14 ultrasonic processor device
16 endoscope processor device
18 light source device
20 monitor
21a water supply tank
21b suction pump
22 insertion portion
24 operating unit
26 universal cord
28a air/water supply button
28b suction button
29 angle knob
30 treatment tool insertion port (forceps port)
32a ultrasound connector
32b endoscope connector
32c light source connector
34a air/water supply tube
34b suction tube
36, 37, 336 ultrasonic observation portion
38, 338 endoscopic observation portion
40, 340 distal end portion
41, 341 exterior member
42 bending portion
43 soft portion
44 treatment tool lead-out port
45 treatment tool channel
46, 69, 75, 246, 294, 346, 369, 375 ultrasonic transducer unit
47, 347 laminated body
48, 348 ultrasonic transducer
50, 350 ultrasonic transducer array
52, 252, 352 electrode portion
52a, 252a, 352a individual electrode
52b, 352b transducer ground
54, 354 backing material layer
coaxial cable
56a signal wire
56b, 56d, 57 jacket
56c shield layer
58, 358 collective ground portion
60, 61, 360 wiring board
62, 362 electrode pad
64, 264, 364 wiring portion
66, 266, 366 connection portion
68, 268, 368 ground bar
70, 71, 370 insulating layer
72, 73, 77, 272, 295, 372, 377 copper foil
74, 374 acoustic matching layer
76, 376 acoustic lens
78 filler layer
80 observation window
82 objective lens
84 solid-state imaging element
86 illumination window
88 cleaning nozzle
89, 308 wiring cable
290a, 290b flexible printed circuit (FPC)
292 ground pad
296a, 296b copper plate
302 annular plate
304 support plate
306 cylindrical member
309 slit
EL longitudinal direction (elevation direction)
AZ parallel direction (azimuth direction)

What is claimed is:

1. An ultrasonic endoscope comprising:
a laminated body that comprises
an ultrasonic transducer array in which a plurality of ultrasonic transducers are arranged, and
a backing material layer that is disposed on a back surface side of the plurality of ultrasonic transducers:
a wiring board that comprises a plurality of electrode pads each of which is electrically connected to a corresponding one of the plurality of ultrasonic transducers of the ultrasonic transducer array;
a plurality of shield cables that comprise
a plurality of signal wires each of which is electrically connected to a corresponding one of the plurality of ultrasonic transducers, and
shield members for the plurality of signal wires;
a wiring portion that comprises a plurality of connection portions at each which a corresponding one of the plurality of signal wires of the plurality of shield cables is electrically connected to a corresponding one of the plurality of electrode pads of the wiring board;
a ground portion that is electrically connected to the shield members of the shield cables and that has heat conductivity; and a first heat conductive member that is disposed on a side surface of the laminated body that comprises the ultrasonic transducer array and the backing material layer, that extends beyond the backing material layer to a side opposite to the ultrasonic transducer array with respect to the backing material layer, and that is thermally connected to the ground portion,
wherein the first heat conductive member is an electro-conductive member,
wherein the wiring board Is disposed on the laminated body side with respect to the first heat conductive member,
wherein, in a region in which the first heat conductive member covers at least the plurality of connection portions of use wiring portion of the wiring board, the ultrasonic endoscope has an insulating layer between the first heat conductive member and the plurality of connection portions,
wherein the insulating layer is formed so as to be affixed along the side surface of the laminated body that comprises the ultrasonic transducer array and the backing material layer and extend beyond the backing material layer to a side opposite to the ultrasonic transducer array with respect to the backing material layer.

2. The ultrasonic endoscope according to claim 1, wherein the first heat conductive member is folded back toward the side surface side of the laminated body and is connected to the ground portion.

3. The ultrasonic endoscope according to claim 1, wherein the insulating layer is removed at least at a portion where the first heat conductive member is connected to the ground portion.

4. The ultrasonic endoscope according to claim 2, wherein the insulating layer is removed at least at a portion where the first heat conductive member is connected to the ground portion.

5. The ultrasonic endoscope according to claim 1, wherein the first heat conductive member has, in a portion extending beyond the backing material layer to the side opposite to the ultrasonic transducer array with respect to the backing material layer, a shape that covers at least a part of a side surface of the wiring board.

6. The ultrasonic endoscope according to claim 2, wherein the first heat conductive member has, in a portion extending beyond the backing material layer to the side opposite to the ultrasonic transducer array with respect to the backing material layer, a shape that covers at least a part of a side surface of the wiring board.

7. The ultrasonic endoscope according to claim 3, wherein the first heat conductive member has, in a portion extending beyond the backing material layer to the side opposite to the ultrasonic transducer array with respect to the backing material layer, a shape that covers at least a part of a side surface of the wiring board.

8. The ultrasonic endoscope according to claim 4, wherein the first heat conductive member has, in a portion extending beyond the backing material layer to the side opposite to the ultrasonic transducer array with respect to the backing material layer, a shape that covers at least a part of a side surface of the wiring board.

9. The ultrasonic endoscope according to claim 1, wherein, in a portion extending beyond the backing material layer to the side opposite to the ultrasonic transducer array with respect to the backing material layer, the first heat conductive member is bent so as to surround the wiring portion and the ground portion and is connected to the ground portion.

10. The ultrasonic endoscope according to claim 1,
wherein the first heat conductive member is an electro-conductive member, and
wherein the first heat conductive member and the ground portion are connected to each other by using a solder or a silver paste.

11. The ultrasonic endoscope according to claim 1, wherein a plurality of the wiring boards are disposed in a portion that is beyond the backing material layer on the side opposite to the ultrasonic transducer array with respect to the backing material layer.

12. The ultrasonic endoscope according to claim 1,
wherein the shield members of the plurality of shield cables are made of a metal, and
wherein the ground portion is a collective ground portion to which the shield members of the plurality of shield cables are electrically connected, a ground bar that is provided in the wiring portion and to which the shield members are electrically connected, or a ground pad that is provided in the wiring board and that is electrically connected to the ground bar.

13. The ultrasonic endoscope according to claim 12, wherein a melting point of a solder that is used to connect the first heat conductive member to the collective ground portion, the ground bar, or the ground pad is lower than a melting point of a solder that is used to connect the collective ground portion, the ground bar, or the ground pad to the shield members of the plurality of coaxial cables.

14. The ultrasonic endoscope according to claim 12,
wherein the ground bar or the ground pad is provided on at least one of a front surface of the wiring board that is a surface on the first heat conductive member side, a back surface of the wiring board that is on a back side of the front surface, or both end surfaces of the front surface and the back surface of the wiring board, and
wherein the first heat conductive member is connected to the ground bar or the ground pad.

15. The ultrasonic endoscope according to claim 12,
wherein a plurality of the wiring boards are disposed in a portion that is beyond the backing material layer on the side opposite to the ultrasonic transducer array with respect to the backing material layer, and
wherein, among the plurality of wiring boards, the ground bars or the ground pads of the wiring boards that are disposed adjacent to each other are thermally connected by using a second heat conductive member that is independent from the first heat conductive member.

16. The ultrasonic endoscope according to claim 12,
wherein a plurality of the wiring boards are disposed in a portion that is beyond the backing material layer on the side opposite to the ultrasonic transducer array with respect to the backing material layer,
wherein at least one of the wiring boards on a central side connects the first heat conductive member to the ground bar or the ground pad on the central side or an end surface side of the wiring board, and
wherein at least one of the wiring boards on an outer side connects the first heat conductive member to the ground bar or the ground pad on the outer side or on an end surface side of the wiring board.

17. The ultrasonic endoscope according to claim 16, wherein, among the plurality of wiring boards, the ground bars or the ground pads of the wiring boards that are disposed adjacent to each other are thermally connected by using a second heat conductive member that is independent from the first heat conductive member.

18. The ultrasonic endoscope according to claim 1, wherein the first heat conductive member is composed of two first heat conductive members that are disposed on both side surfaces of the laminated body and that are connected to each other by using a third heat conductive member.

* * * * *